US011076764B1

(12) United States Patent
Goubran et al.

(10) Patent No.: US 11,076,764 B1
(45) Date of Patent: Aug. 3, 2021

(54) PRESSURE SENSITIVE MAT SYSTEM WITH DYNAMICALLY CALIBRATABLE PRESSURE SENSORS AND METHOD FOR NON-OBTRUSIVE MONITORING OF VITAL SIGNS AND OTHER HEALTH METRICS

(71) Applicant: Press-IR Inc., Ottawa (CA)

(72) Inventors: Rafik Alphonse Goubran, Ottawa (CA); Frank-Dietrich Knoefel, Nepean (CA); Raymond Bruce Wallace, Ottawa (CA)

(73) Assignee: Press-IR Inc., Ottawa (CA)

( * ) Notice: Subject to any disclaimer, the term of this patent is extended or adjusted under 35 U.S.C. 154(b) by 0 days.

(21) Appl. No.: 17/001,284

(22) Filed: Aug. 24, 2020

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/1102* (2013.01); *A61B 5/113* (2013.01);
(Continued)

(58) Field of Classification Search
CPC ................ A61B 5/6892; A61B 5/1102; A61B 5/113–1135; A61B 2562/04–046; A61B 2562/0247; A61B 2562/0257
See application file for complete search history.

(56) References Cited

U.S. PATENT DOCUMENTS

| 4,711,246 A | 12/1987 | Alderson |
| 4,926,696 A | 5/1990 | Haritonidis et al. |

(Continued)

FOREIGN PATENT DOCUMENTS

| EP | 0090126 B1 | 9/2002 |
| WO | 2017093485 A2 | 6/2017 |

OTHER PUBLICATIONS

Selzler et al. "Developing a pressure sensitive mat using proximity sensors for vital sign monitoring," 2018 IEEE International Instrumentation and Measurement Technology Conference (I2MTC), Houston, TX, 2018, pp. 1-5. (Year: 2018).*
(Continued)

*Primary Examiner* — Meredith Weare
(74) *Attorney, Agent, or Firm* — Borden Ladner Gervais LLP; Louis B. Allard

(57) ABSTRACT

System and method that use a pressure sensitive mat to monitor vitals signs of an individual positioned on the pressure sensitive mat. The pressure sensor mat is coupled to pressure sensors that each have an adjustable pressure responsivity. In order to be able to monitor the vital signs without interruption due to the individual repositioning themself on the pressure sensitive mat and thereby running the risk of increasing the pressure on some pressure sensors to the point of saturation, or running the risk of decreasing the pressure on other pressure sensors to the point losing any usable signal, the system comprises circuitry that monitors a baseline pressure sensor at one pressure sensor and controls, as a function of the monitored signal, the pressure responsivity at a neighbor pressure sensor. This allows the neighbor sensor to generate a monitored signal with discernable time dependent features associated with the individual's vital signs.

18 Claims, 14 Drawing Sheets

(51) Int. Cl.
*A61B 5/113* (2006.01)
*A61B 5/11* (2006.01)

(52) U.S. Cl.
CPC .............. *A61B 5/6892* (2013.01); *A61B 5/72* (2013.01); *A61B 2560/0223* (2013.01); *A61B 2562/0247* (2013.01); *A61B 2562/0257* (2013.01); *A61B 2562/04* (2013.01)

(56) References Cited

U.S. PATENT DOCUMENTS

| | | | |
|---|---|---|---|
| 5,917,180 A * | 6/1999 | Reimer | G01L 1/24 250/227.14 |
| 2002/0092356 A1 | 7/2002 | Yamamoto et al. | |
| 2004/0031326 A1 | 2/2004 | Lenzing et al. | |
| 2004/0046668 A1 | 3/2004 | Smith et al. | |
| 2008/0132808 A1 | 6/2008 | Lokhorst et al. | |
| 2013/0109931 A1 | 5/2013 | Ng et al. | |
| 2015/0285699 A1 | 10/2015 | Brinciotti et al. | |
| 2016/0357296 A1* | 12/2016 | Picciotto | G06F 3/016 |
| 2017/0010164 A1 | 1/2017 | Qian | |
| 2017/0261607 A1 | 9/2017 | Bridge et al. | |
| 2017/0333274 A1* | 11/2017 | Riley | A61B 5/02055 |
| 2018/0306638 A1* | 10/2018 | Ishikawa | G01J 3/0229 |

OTHER PUBLICATIONS

Selzler, Roger. "Development of a Novel Pressure-Sensitive Mat Using Proximity Sensors." Master's Thesis, Carleton University, 2018. (Year: 2018).*

"Average." Wikipedia. Jul. 31, 2019. https://web.archive.org/web/20190731225740/https://en.wikipedia.org/wiki/Average (Year: 2019).*

* cited by examiner

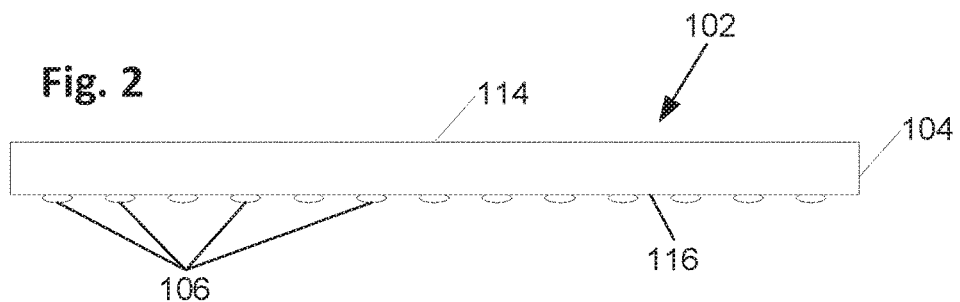
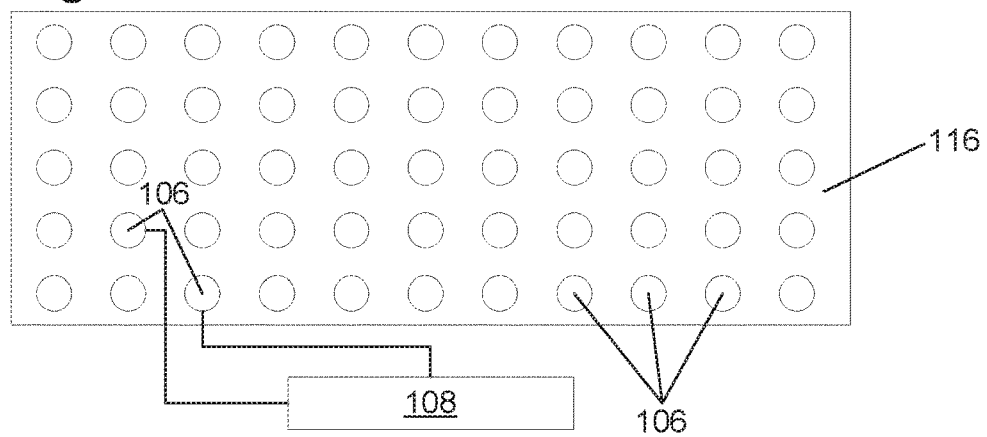
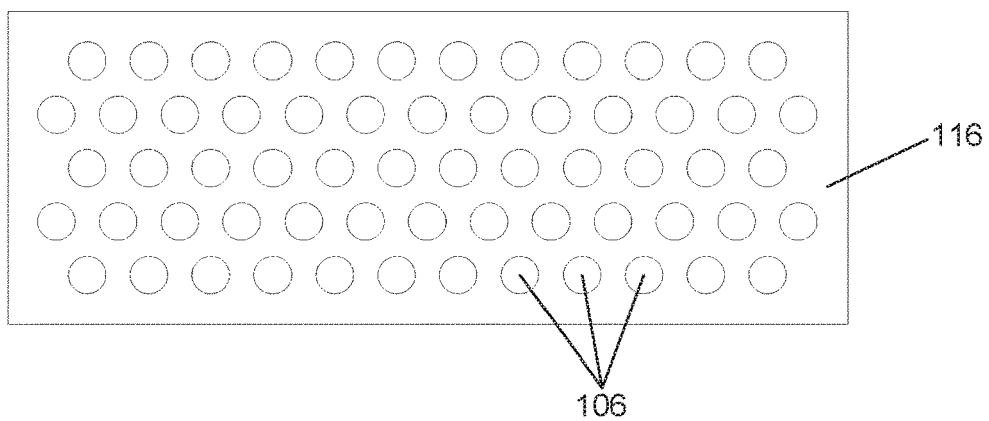

PRESSURE SENSITIVE MAT SYSTEM WITH DYNAMICALLY CALIBRATABLE PRESSURE SENSORS AND METHOD FOR NON-OBTRUSIVE MONITORING OF VITAL SIGNS AND OTHER HEALTH METRICS

FIELD OF THE INVENTION

The present invention relates generally to non-obtrusive monitoring of an individual's vital signs, symptoms and other health metrics. In particular, the present invention relates to non-obtrusive monitoring of vital signs, symptoms and other health metrics using pressure sensitive mats.

BACKGROUND OF THE INVENTION

Different systems for non-obtrusive monitoring of an individual's vital signs or other health metrics have been developed and are the subject of active research. Some of these approaches use pressure-sensitive mats (PSM) for monitoring the vital signs of an individual positioned on the PSM, which measures the spatial distribution of pressure applied by the individual to the PSM and the variation over time of the applied pressure. Such time dependent measurements can be used to measure vital signs such as the breathing rate and the heart rate of the individual. Another vital sign that can be monitored using PSMs is the movement of fluid in an individual as a function of time.

Different technologies using electrical (resistive, piezoresistive, capacitive), mechanical or optical pressure sensors have been used in PSMs and have been shown to have strength and weaknesses with respect to their measurement capabilities. A common problem with PSMs and the underlying technologies is their limited versatility with respect to the monitoring of vital signs of individuals having different weights and body types, and with respect to reliably monitor low intensity signals associated with vital signs of the individual as the individual changes their position on the PSM.

Improvements in PSMs are therefore desirable.

SUMMARY OF THE INVENTION

In a first aspect, the present invention provides a system for monitoring health metrics of an individual. The system comprises a mat; a plurality of pressure sensors coupled to the mat, the plurality of pressure sensors configured to generate a respective plurality of pressure signals when the individual is positioned on the mat and applies a pressure to the mat, each pressure sensor of the plurality of pressure sensors having a respective pressure responsivity configured to be modified by varying an electrical parameter of the respective pressure sensor; circuitry coupled to the plurality of pressure sensors. The circuitry is configured to: monitor a first pressure signal generated by a first pressure sensor of the plurality of pressure sensors, to obtain a first monitored signal; in accordance with the first monitored signal and in accordance with pre-determined rules, vary the electrical parameter of a second pressure sensor of the plurality of pressure sensors, to obtain a modified pressure responsivity; and monitor a second pressure signal generated by the second pressure sensor that has the modified pressure responsivity, the monitored second pressure signal being associated with at least one of the health metrics of the individual.

In some embodiments of the first aspect, the circuitry is configured to vary the electrical parameter of the second pressure sensor in accordance with the first monitored signal and in accordance with the pre-determined rules by analyzing the first monitored signal to obtain an analysis result and by evaluating the analysis result in accordance with the pre-determined rules. Analyzing the first monitored signal may include calculating an average value of the first monitored signal, and the analysis result may the average value. In some embodiments, calculating an average value includes at least one of calculating: an arithmetic mean value; a median value; and a mode value.

In some embodiments, analyzing the first monitored signal may include calculating a derivative of the first monitored signal as a function of time to obtain a derivative value; and the analysis result may be the derivative value.

In some embodiments, the circuitry may be further configured to filter out of the first pressure signal, frequencies above a frequency threshold.

In some embodiments, the mat has a top surface and the plurality of pressure sensor are arranged in a pattern that is substantially parallel to the top surface. The pattern may be a square pattern or a hexagonal pattern.

In some embodiments, the mat has a top surface and the plurality of pressure sensors are spaced apart from, and substantially parallel to, the top surface.

In some embodiments, the mat may have two or more than two portions that have a different areal density of pressure sensors.

In some embodiments, each pressure sensor of the plurality of pressure sensors may include a proximity sensor assembly with a light emitter and a light detector, the electrical parameter of each pressure sensor being a current of the light emitter. The light emitter may be configured to emit infrared light and the light detector may be configured to detect infrared light. The mat may have a top layer configured to reflect light emitted by the light emitter; a compressible layer coupled to the top layer, the compressible layer configured to be compressed upon pressure being applied thereto and further configured to transmit the light emitted by the light emitter; and a bottom layer coupled to the compressible layer and spaced apart from the top layer by the compressible layer, the bottom layer having the plurality of pressure sensors secured thereto. The bottom layer may define a plurality of recesses, each recess of the plurality of recessed having a pressure sensor of the plurality of sensor secured therein.

The plurality of pressure sensors may include a first group of pressure sensors and a second group of pressure sensors, and, when the individual is not applying pressure on the mat, each pressure sensor of the first group of pressure sensors is spaced apart from the top layer by a first distance, each pressure sensor of second group of pressure sensors being spaced apart from the top layer by a second distance, the second distance being different from the first distance. The first distance may be greater than the second distance, the first distance being equal to a thickness of the compressible layer between the top layer and each pressure sensor of the first group of pressure sensors, and the second distance being equal to a thickness of the compressible layer between the top layer and each pressure sensor of the second group of pressure sensors.

The monitored second pressure signal may be associated with at least one of the heart rate of the individual and the breathing rate of the individual.

The circuitry may be further configured to, in accordance with the first monitored signal and in accordance with pre-determined rules, vary the electrical parameter of additional pressure sensors of the plurality of pressure sensors, to obtain a modified pressure responsivity; and monitor additional pressure signals generated by the additional pressure sensors that have the modified pressure responsivity, the monitored additional pressure signals also being associated with the at least one of the vital sign of the individual.

The circuitry may configured to calibrate the plurality of pressure sensors to a weight of the individual when the individual is positioned on the mat, by performing the following actions: monitoring a pressure signal generated by each pressure sensor of the plurality of pressure sensors, to obtain a plurality of monitored signals; and in accordance with the plurality of monitored signals and in accordance with pre-determined rules, vary the electrical parameter of each pressure sensor of the plurality of pressure sensors, to obtain a modified pressure responsivity for each pressure sensor of the plurality of pressure sensors.

In some embodiments, the predetermined rules are set to obtain, for each pressure sensor of the plurality of pressure sensors, a respective modified pressure responsivity that causes each respective pressure sensor to generate a signal that is equal to a pre-determined ratio of a full signal range of the respective pressure sensor. The pre-determined ratio may be equal to 0.5.

In some embodiments, The circuitry may include: a pressure sensor interface coupled to the plurality of pressure sensors; a pressure sensor monitor coupled to the pressure sensor interface, the pressure sensor monitor to monitor the plurality of pressure signals, to determine when to modify the pressure responsivity of the plurality of pressure sensors, and to generate a plurality of control signals associated with a modification of the pressure responsivity of each of the plurality of pressure sensors; and a controller coupled to the pressure monitor and to the pressure sensor interface, the controller to control the electrical parameter of each of the plurality of the pressure sensors, in accordance with the plurality of control signals.

In another aspect, the present disclosure provides a system for monitoring vital signs of an individual, the system comprising: a mat; a plurality of pressure sensors coupled to the mat, the plurality of pressure sensors configured to generate a respective plurality of pressure signals when the individual applies a pressure on the mat, each pressure sensor of the plurality of pressure sensors having a respective pressure responsivity configured to be modified by varying an electrical parameter of the respective pressure sensor; circuitry coupled to the plurality of pressure sensors, the circuitry configured to: monitor a pressure signal generated by each pressure sensor of the plurality of pressure sensors, to obtain a plurality of monitored signals; in accordance with the plurality of monitored signals and in accordance with pre-determined rules, vary the electrical parameter of each pressure sensor of the plurality of pressure sensors, to obtain a modified pressure responsivity for each pressure sensor of the plurality of pressure sensors; and monitor a pressure signal generated by the each pressure sensor of the plurality of pressure sensors subsequent a modification of the pressure responsivity of each pressure sensor of the plurality of pressure sensors.

In a further aspect, the present disclosure provides A system for monitoring vital signs of an individual, the system comprising: a mat; a plurality of pressure sensors coupled to the mat, the plurality of pressure sensors configured to generate a respective plurality of pressure signals when the individual applies a pressure on the mat, each pressure sensor of the plurality of pressure sensors having a respective pressure responsivity is equal to a multiple of the pressure responsivity of a neighbor pressure sensor or is equal to a sub-multiple of the pressure responsivity of the neighbor pressure sensor; and circuitry coupled to the plurality of pressure sensors, the circuitry configured to monitor a pressure signal generated by each pressure sensor of the plurality of pressure sensors, to obtain a plurality of monitored signals associated with at least one of the vital sign of the individual.

In yet a further aspect, the present disclosure provides a method of monitoring vital signs of an individual, the method comprising: when the individual is positioned on a pressure sensitive mat that comprises a plurality of pressure sensors, the plurality of pressure sensors configured to generate a respective plurality of pressure signals when the individual is positioned on the mat, each pressure sensor of the plurality of pressure sensors having a respective pressure responsivity configured to be modified by varying an electrical parameter of the respective pressure sensor, monitor a first pressure signal generated by a first pressure sensor of the plurality of pressure sensors, to obtain a first monitored signal; in accordance with the first monitored signal and in accordance with pre-determined rules, vary the electrical parameter of a second pressure sensor of the plurality of pressure sensors, to obtain a modified pressure responsivity; and monitor a second pressure signal generated by the second pressure sensor that has the modified pressure responsivity, the monitored second pressure signal being associated with at least one of the vital sign of the individual. Varying the electrical parameter of a second pressure sensor of the plurality of pressure sensors in accordance with first monitored signal and in accordance the pre-determined rules may include: analyzing the first monitored signal to obtain an analysis result; and evaluating the analysis result in accordance with the pre-determined rules. Analyzing the first monitored signal may include calculating an average value of the first monitored signal, the analysis result being the average value. Calculating the average value may include at least one of calculating: an arithmetic mean value; a median value; and a mode value. Analyzing the first monitored signal may include: calculating a derivative of the first monitored signal as a function of time to obtain a derivative value, the analysis result being the derivative value.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures.

FIG. 2 shows a side elevation view of an embodiment of a pressure sensitive mat in accordance with the present disclosure.

FIG. 3 shows a bottom view of the pressure sensitive mat of FIG. 2.

FIG. 4 shows a bottom view of another embodiment of a pressure sensitive mat in accordance with the present disclosure.

DETAILED DESCRIPTION

Generally, the present disclosure provides a system for non-obtrusive monitoring of vital signs, symptoms and other health metrics of an individual. The vital signs can include, for example, the individual's heart rate or breathing rate. Such vital signs result in periodic pressure variations, often small pressure variations, in the individual's body. Symptoms that can be monitored include those associated with illnesses where fluid accumulates in an individual's lower limbs when the individual is upright, and re-distribute themselves in the individual's body when the individual lies down. Other health metrics than can be monitored may include the mobility of the individual (i.e., the individual's ability to move), the frequency at which the individual reposition themself, involuntary movement of the individual's limbs, the symmetry of the individual's movements as the individual moves to get out of bed, etc.

The present disclosure describes systems that comprise a PSM on which the individual whose health metrics (e.g. vital signs, symptoms, etc.) are being monitored can be positioned. The PSM has pressure sensors coupled thereto. The pressure sensors are used to monitor the pressure applied to the PSM as a function of time. Embodiments of systems in accordance with the present disclosure further comprise a controller and a pressure monitor coupled to the pressure sensors. The pressure sensors can be individually controlled by the controller as a function of the monitored pressure applied to the PSM. The control of the pressure sensors is a control of the pressure responsivity and/or the pressure range of each individual pressure sensor. That is, the pressure sensors are dynamically calibratable in the sense that their pressure responsivity and/or pressure range can be controlled while the individual's health metrics are being monitored.

In some embodiments, the controller can adjust the pressure sensitivity of a first pressure sensor in accordance with the variations in pressure monitored at a second pressure sensor. In doing so, a substantial variation in pressure at the first pressure sensor, caused, for example, by the individual repositioning themselves on the PSM, can be used to adjust the pressure sensitivity of the second pressure sensor, which is used to monitor small variations in the pressure cause by vital signs or symptoms or other health metric of the individual. If the change in pressure detected at the first pressure sensor is a positive change, i.e., the monitored pressure shows an increase, the pressure sensitivity of the second pressure sensor can be reduced, if need be, such that the signal at the second pressure sensor is not saturated but still shows a time dependent component, attributable to a least one health metric.

Figure 1:
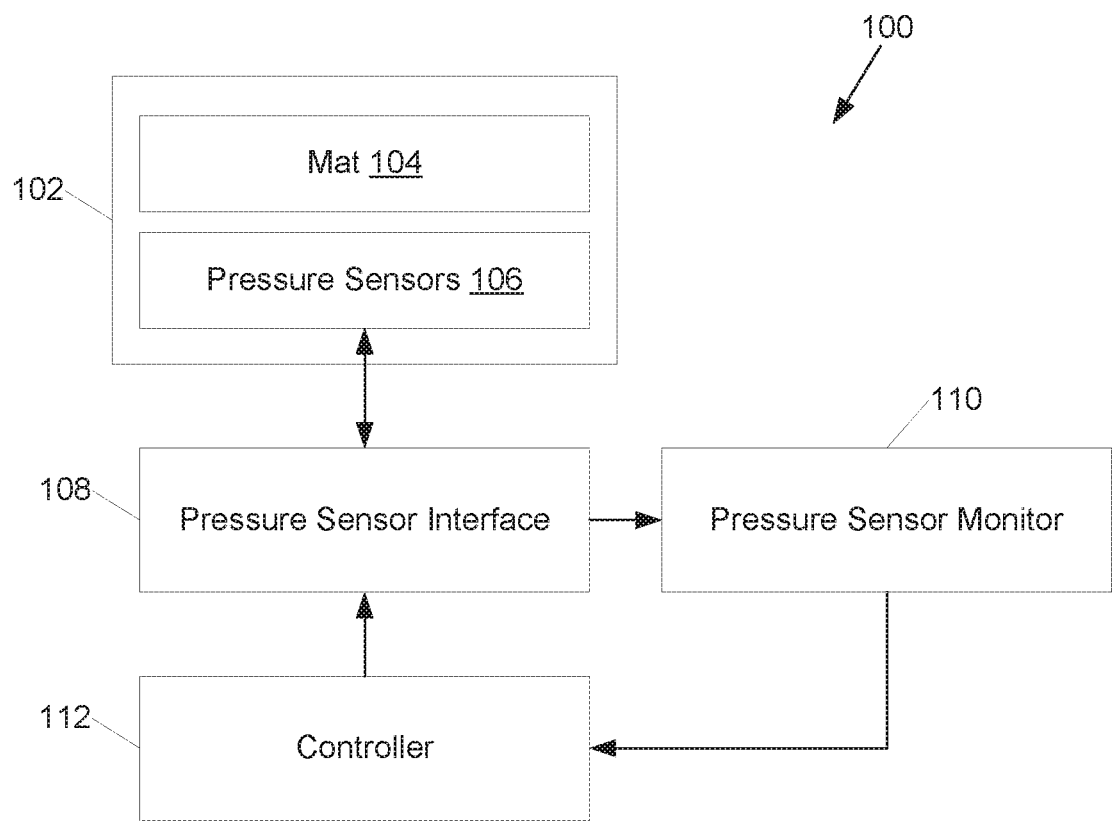
FIG. 1 shows a block diagram of an embodiment of a system in accordance with the present disclosure.

FIG. 1 shows a block diagram of an embodiment of a system 100 for monitoring vital signs or other health metric of an individual, in accordance with the present disclosure. The system 100 has a pressure sensitive mat 102, which comprises a mat 104 and pressure sensors 106 coupled to the mat 104. The coupling between the mat 104 and the pressure sensors 106 is such that an application of pressure on the top surface of the mat 104 results in pressure being applied to the pressure sensors 106. Depending on the amount of pressure being applied and on the location of the top surface of the mat 104 at which the pressure is applied, some of the pressure sensors 106 may be subjected to a pressure attributable to the positioning of the individual on the mat 104, while other pressure sensors 106 may not.

The system 100 comprises a pressure sensor interface 108 connected to pressure sensors 106 as well as to a pressure sensor monitor 110 and to a controller 112. Although shown as separate components, the pressure sensor interface 108, the pressure sensor monitor 110 and the controller 112 can all be part of a same module or device. Or, in other embodiments, only some of the pressure sensor interface 108, the pressure sensor monitor 110 and the controller 112 can be part of a same module of device. The pressure sensor interface 108, the pressure sensor monitor 110 and the controller 112 can be referred to as circuitry coupled to the pressure sensors 106.

Upon an individual applying pressure to the mat 104 and to the pressure sensors 106, the pressure sensor interface obtains measured pressure values from the pressure sensors 106 and provides the measured pressure values to the pressure sensor monitor 110. The pressure sensor monitor 110 determines if any of the pressure sensors 106 need to have their pressure sensitivity adjusted and, if some of the pressure sensors 106 do, the pressure sensor monitor 110 provides, to the controller 112, an identification of which pressure sensor 106 or pressure sensors 106 that need to have their pressure sensitivity adjusted and by how much the respective pressure sensitivity should be adjusted. In turn, the controller 112 generates control signals that are communicated, via the pressure sensor interface 108, to the pressure sensors 106 that require pressure sensitivity adjustment. The control signals are to control an electrical parameter of the pressure sensors. Details regarding various examples of pressure sensitivity adjustment are provided further below.

The mat 104 can be of any suitable size, such as, for example a size comparable to bed surface or a size comparable to a chair's seat and/or backrest. The mat can be made of any suitable material, such as, for example, a silicone rubber epoxy. The pressure sensors 106 can be of any type, provided they have a controllable pressure sensitivity.

Examples of such pressure sensors include, as examples, pressure sensors based on proximity sensors, pressure sensors based on force sensitive resistors (FSRs), pressure sensors based fibre optics. The pressure sensor interface 108, the pressure sensor monitor 110 and the controller 112 can be of any suitable types. For example, the sensor interface 108 can include, for example, an Inter-Integrated Circuit (I²C) bus, a universal asynchronous receiver-transmitter (UART) bus, a universal serial bus (USB) or a serial peripheral interface (SPI) bus. The sensor interface 108 can also include a multiplexer coupled to each pressure sensor 106 in the mat 104, to the bus (I2C, UART, USB or SPI). The pressure sensor monitor 110 and the controller can be any suitable computing device that couples to the sensor interface 108.

FIG. 2 shows a side elevation view of an embodiment of a PSM 102 in accordance with the present disclosure. The PSM 102 has a mat 104 with a top surface 114 and a bottom surface 116. The PSM 102 has a plurality of pressure sensors 106 coupled to the bottom surface 116. The mat 104 is constructed such that pressure applied to the top surface 114 is felt on the pressure sensors 106, through the mat 104 and the back surface 116. As such, the pressure sensors 106 are coupled to the mat and to the top surface 114.

FIG. 3 shows a bottom view of the PSM 102 of FIG. 2. FIG. 3 shows the pressure sensors 106 and the back surface 116. FIG. 3 also shows operational connections 118 of the pressure sensors 116 to the pressure sensor interface 108. Although only two operational connections 118 are shown, it is to be understood that each pressure sensor 106 is connected to the pressure sensor interface 108. The expression "operational connection" is to be understood as meaning electrical connections, optical connections, wireless connections or combinations thereof. The operational connections 106 couple the pressure sensors 106 to the pressure sensor interface 108.

The embodiment of FIG. 3 shows the pressure sensors 106 equi-spaced from each other in a square pattern. However, the pressure sensors 106 can be distributed in any suitable pattern and do not need to be equi-spaced from each other. For example, FIG. 4 shows a bottom view of another embodiment of the PSM 102 where the pressure sensors 106 are arranged in a hexagonal pattern. In the hexagonal pattern, each pressure sensor 106 is spaced-apart from six nearest neighbors, by the same distance. The pressure sensors 106 can be connected to the bottom surface 116 in any suitable way. For example, the pressure sensors 106 can be adhered to the bottom surface 116 using any suitable glue layer. The bottom surface 116 can also define interference elements (e.g., protrusions, indentations, etc.) between which the pressure sensors 106 can be held in place. Although the pressure sensors 106 are shown as having a circular shape, it is to be understood that they can have any other suitable shape (e.g. square, diamond, hexagon, etc.)

In some embodiments, there may be a higher density of pressure sensors 106 in some portions of the PSM 102 and a lower density of pressure sensors in other portions of the PSM 103. In some cases, the higher density of pressure sensors 106 can be in a portion of the PSM 102 where the trunk of an individual is likely to be positioned when the individual lies on the PSM 102. The lower density of pressure sensors 106 can be in portions of the PSM 102 where the limbs or head of the individual are likely to rest when the individual lies on the PSM 102. This arrangement of pressure sensors 106 allows for a higher spatial density of pressure sensors 106 in an area of the body, namely the trunk, which is likely to be of high interest as it is the source of the individual's heartbeat and breathing.

Figure 5:
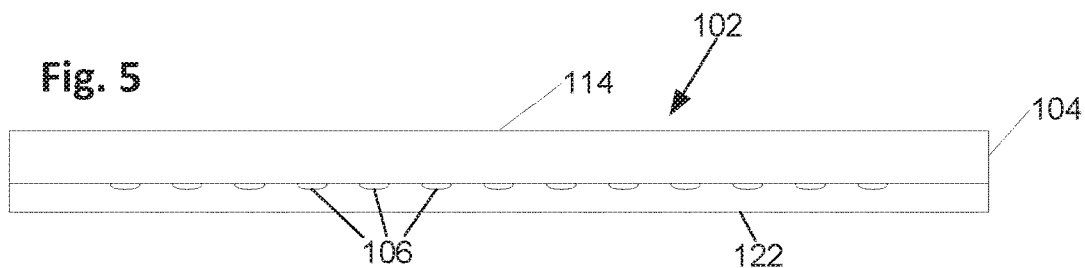
FIG. 5 shows a side elevation view of another embodiment of a pressure sensitive mat in accordance with the present disclosure.
Figure 6:
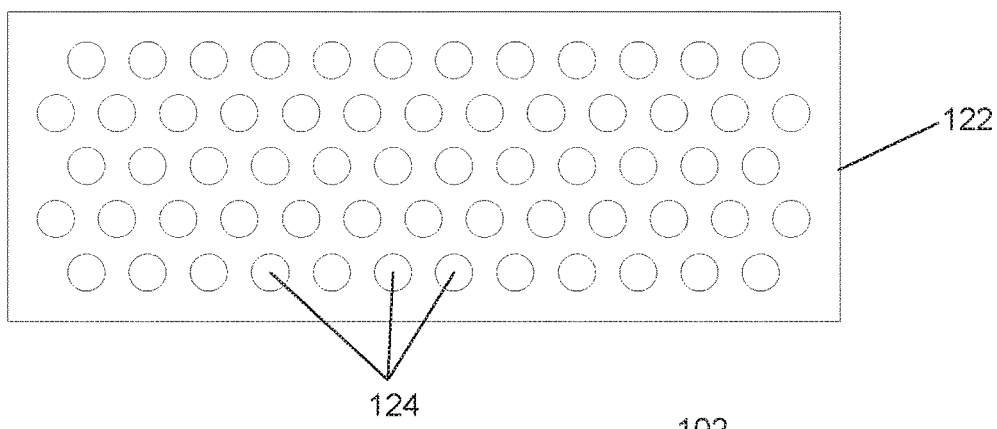
FIG. 6 shows a top view of a bottom layer of the pressure sensitive mat of FIG. 5.

FIG. 5 shows a side elevation view of an embodiment of a PSM 102 in accordance with the present disclosure. In this embodiment, the PSM 102 has a mat 104 coupled to a bottom layer 122 in which the pressure sensors 106 are embedded. The bottom layer 122 can have a series of recesses defined therein and, the pressure sensors 106 are positioned in the recesses and can be secured therein through any suitable means. FIG. 6 shows a top view of the bottom layer 122 and of recesses 124 configured to receive the pressure sensors. The bottom layer 122 can be made of any suitable material such as, for example, silicone rubber.

Figure 7A:
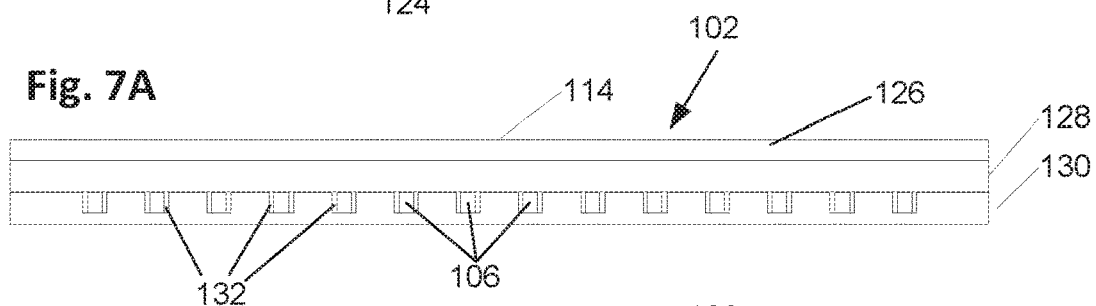
FIG. 7A show a side, cross-sectional view of another embodiment of a pressure sensitive mat in accordance with the present disclosure.

FIG. 7A show a side, cross-sectional view of an embodiment of a PSM 102 in accordance with the present disclosure. In the embodiment of FIG. 7A, the PSM 102 has a top layer 126 with a top surface 114, a compressible layer 128, and a bottom layer 130, which defines a series of recesses 132. Each recess 132 has a pressure sensor 106 located therein. In the some embodiments, the pressure sensors 106 are proximity pressure sensor assemblies (PPSAs).

An advantage of using PPSAs is they can be manufactured to have a small footprint, e.g., 1 cm$^2$, in comparison with other pressure sensors such as, for example, fiber optic sensors (~5 cm in diameter) or FSR assemblies (~2 cm$^2$).

Figure 8:
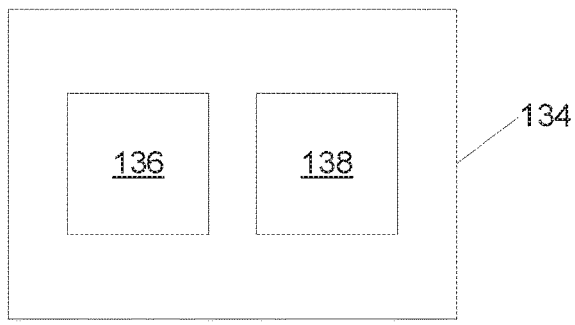
FIG. 8 shows a top view of an embodiment of a proximity pressure sensor assembly in accordance with the present disclosure.

A top view of a PPSA 134 is shown in FIG. 8. The PPSA 134 has a light emitter 136 and a light detector 138. The light emitter 136 can be an infrared light emitter and the light sensor can be an infrared light sensor. Light emitters and detectors configured for operation at wavelengths other than the wavelengths in the infrared portion of the electromagnetic spectrum can also be used.

Referring back to FIG. 7A, the compressible layer 128 is made of compressible material that is transparent, or at least partially transparent, to the light emitted by the light emitter 136. The material of which the compressible layer 128 is made can be a medium firmness clear silicone gel (for example, Smooth-On™ resins or MG Chemicals™ potting compounds). The top layer 126 can be made of a material that reflects the light emitted by the light emitter 136. For example, the top layer can be made of a medium firmness white silicone gel (for example, Smooth-On™ resins or MG Chemicals™ potting compounds). In the embodiment of FIG. 7A, the pressure sensors are all separated from the top layer 126 by a same distance.

The top layer 126, the compressible layer 128 and the bottom layer 130 can be formed in any suitable way. For example, in some embodiments, the compressible layer may be manufactured as a unit and subsequently placed atop the pressure sensors 106 and the bottom layer 130. In other embodiments, a liquid silicone gel can be poured on top of the pressure sensors 106 and the bottom layer 130, and subsequently be left to solidify and become the compressible layer.

Figure 7B:
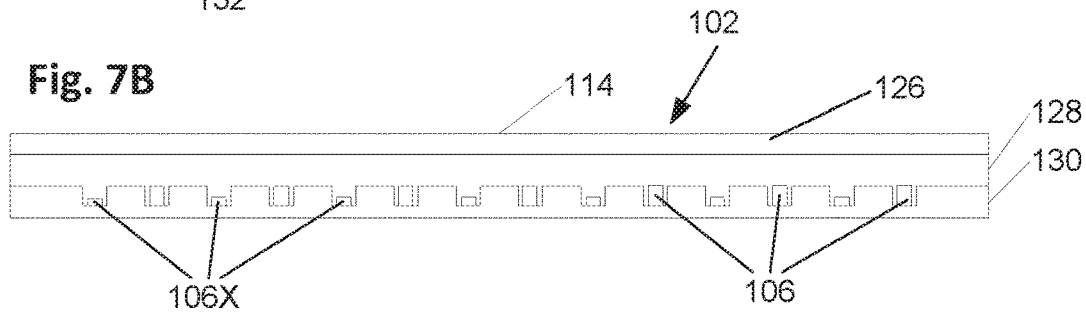
FIG. 7B show a side, cross-sectional view of another embodiment of a pressure sensitive mat in accordance with the present disclosure.

FIG. 7B shows a side, cross sectional view of another embodiment of a PSM 102 in accordance with the present disclosure. In the embodiment of FIG. 7A, some of the pressure sensors (pressure sensors 106X) are spaced apart from the top layer 126 by a greater distance than some of the other pressure sensors 106. As the pressure sensors 106X are separated from the top layer by a larger thickness of compressible material, they can withstand more pressure before saturating than the other pressure sensors 106 that are separated from the top layer 126 by a smaller thickness of compressible material. Any arrangement where some of pressure sensors have a larger amount of compressible material separating them from the top layer than other pressure sensors is to considered within the scope of the present disclosure.

Figure 9:
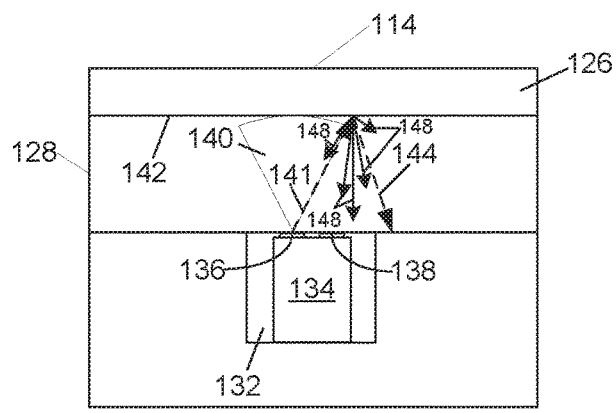
FIG. 9 shows a side elevation view of a portion of the pressure sensitive mat of FIG. 7A.

FIG. 9 shows a side elevation view of a portion of the PSM 102 of FIG. 7A. FIG. 9 shows a recess 132 having a PPSA 134 disposed therein. The light emitter 136 is shown emitting a cone of light 140 upwardly, the cone of light 140 comprising a plurality of light beams. In that cone of light 140 is a light ray 141, shown as an example, that traverses the compressible layer 128 and reflects off the bottom surface 142 of the top layer 126. The light beam 141 can be thought of as a plurality of light rays that are each reflected off the bottom surface 142 in accordance with the law of reflection. As will be understood by the worker skilled in the art, the individual light rays that make up the light beam 141 can be absorbed to some extent in the compressible layer 148, or transmitted to some extent in the top layer 126, depending on the material of the top layer 126, the material of the compressible layer 128, the angle of incidence of the individual light rays on the bottom surface 142, and the wavelength of the light rays. Some of the reflected light reaches the light detector 138, which gives rise to an electrical signal. The arrow 144 in FIG. 9 represents a specular reflection of the light beam 141. In FIG. 9, no external pressure is applied to the top surface of 114 of the top layer 126.

Figure 10:
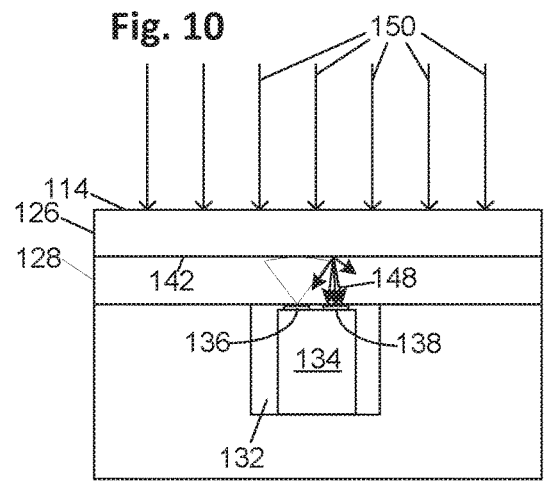
FIG. 10 shows the same view as in FIG. 9 but in a scenario where external pressure is applied to the pressure sensitive mat.

FIG. 10 shows the same view as that shown in FIG. 9, but in a scenario where external pressure is applied to the top surface 114 of the top layer 126. The external pressure is represented by the arrows 150. In FIG. 10, the pressure applied to the top surface 114 causes a compression of the compressible layer 128, which shortens the distance between the bottom surface 142 and the PPSA 134. Because of the shortened distance, more reflected light reaches the light detector 138 in the scenario of FIG. 10 than in the scenario shown at FIG. 9, where no pressure is applied to the top surface 114.

Figure 11:
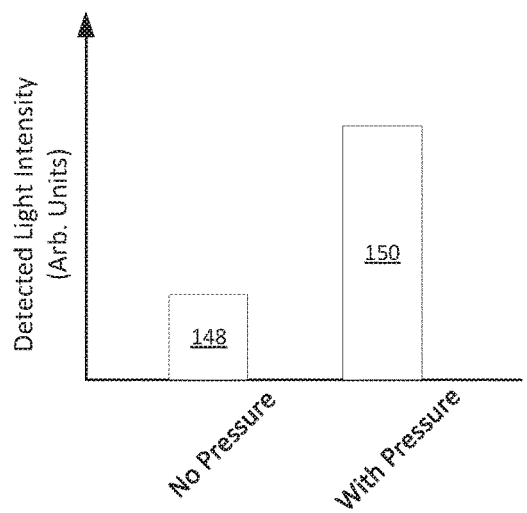
FIG. 11 shows a bar graph with a first bar that represents the detected light intensity when no pressure is applied to the pressure sensitive mat shown partially in FIG. 9 and a second bar that represents the detected light intensity when there is pressure applied to the pressure sensitive mat shown partially in FIG. 10.

FIG. 11 shows a bar graph with a first bar 148 that represents the detected light intensity when no pressure is applied to the PSM 102 (scenario shown in FIG. 9) and a second bar 150 that represents the detected light intensity when there is pressure applied to the PSM (scenario shown in FIG. 10).

Figure 12:
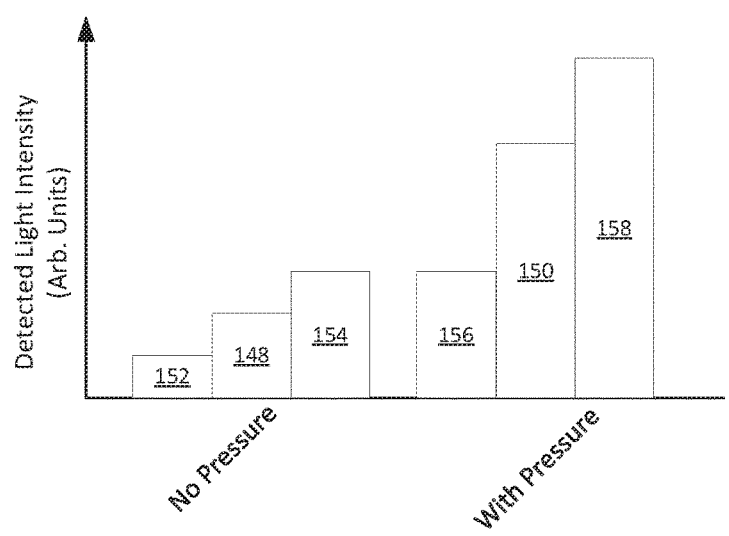
FIG. 12 shows a bar graph with three bars that represent the detected light intensity for three different pressure responsivity setting when no pressure is applied to the pressure sensitive mat of FIG. 9 and three bars that represent the detected light intensity for three different pressure responsivity settings when pressure in applied to the pressure sensitive mat shown in FIG. 10.

The PPSA 134 has a controllable pressure sensitivity in that the light intensity of the light emitter 136 can be adjusted by controlling the current powering the light emitter 136, the current being an electrical parameter of the PPSA 134. FIG. 12 shows a bar graph with the same bars 148 and 150 as those shown in FIG. 11. FIG. 12 also shows bars 152 and 156, which represent the detected light intensity when the light intensity of the light emitter 136 is reduced, (by reducing the electrical current) with respect to the light intensity level used when detecting the light intensity represented by bars 148 and 150 respectively. FIG. 12 also shows bars 154 and 158, which represented the detected light intensity when the light intensity of the light emitter 136 is increased (by increasing the electrical current) with respect to the light intensity level used when detecting the light intensity represented by bars 148 and 150 respectively. The pressure sensitivity is lowest in the cases represented by bars 152 and 156. The pressure sensitivity is greatest in the cases represented by bars 154 and 158.

Figure 13:
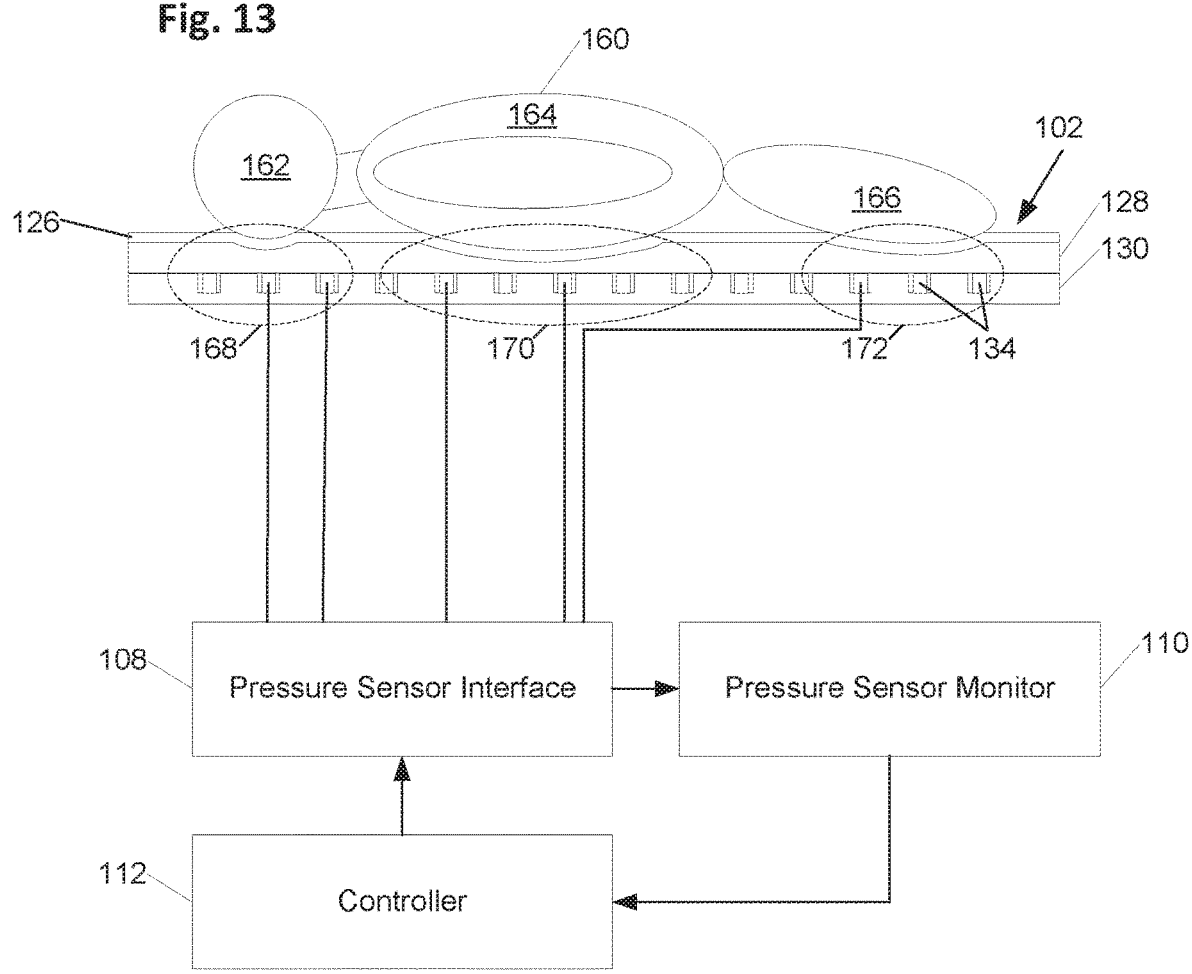
FIG. 13 shows an embodiment of the present disclosure where an individual lies on the pressure sensitive mat of FIG. 7A.

FIG. 13 shows an embodiment of the present disclosure where an individual 160 lies on the PSM 102 embodiment of FIG. 7A. The individual's head 162, trunk 164 and legs 166 lie on respective portions 168, 170 and 172 of the PSM 102 and can apply different pressures to these different portions. In the embodiment of FIG. 13, the trunk 164 applies more pressure to the portion 170 than the legs 166 apply pressure to the portion 172. The head 162 applies less pressure to the portion 168 than the legs 166 apply pressure to the portion 172. That is to say, the compressible layer 128 is more compressed in the portion 170 than it is in the portion 172. The compressible layer 128 is less compressed in the portion 168 than in the portion 172. The PPSAs 134 are coupled to the pressure sensor interface 108, which is coupled to the pressure sensor monitor 110 and to the controller 112. For clarity purposes, only some of the PPSAs 134 are shown as being coupled to the interface 108.

In situations where the individual is sufficiently heavy to apply a pressure in the portion 170 that causes the PPSAs 134 in the portion 170 to have a saturated detected light intensity, the pressure sensitivity of the saturated PPSAs 134 can be reduced by decreasing the light intensity generated by the respective light emitters 136. To do so, the pressure sensor monitor 110 is configured to detect which PPSAs 134 are experiencing saturated light detectors 138. The pressure monitor sensor 110 can subsequently instruct the controller 112 to decrease the pressure sensitivity of the PPSAs 134 that are experiencing saturation by reducing the electrical current powering the emitter 136 of the PPSAs 134.

Figure 14:
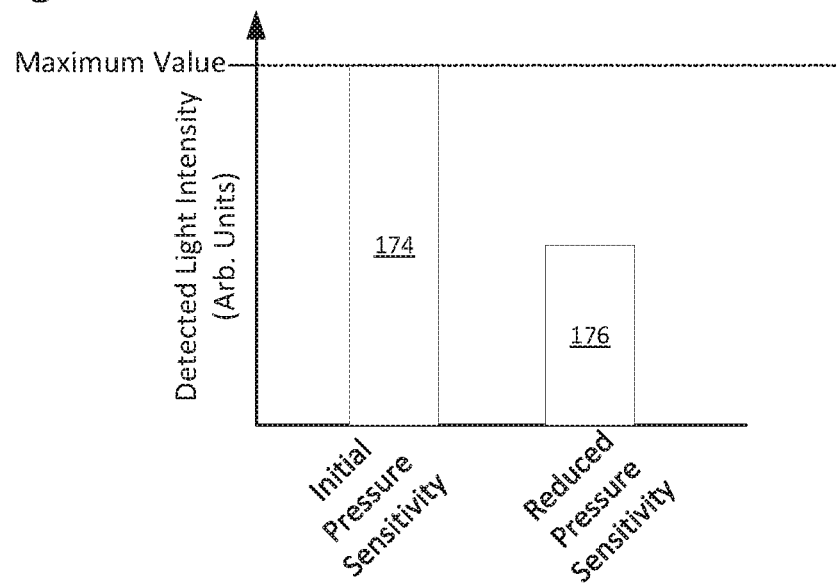
FIG. 14 shows a bar graph with a first bar that represents the saturated detected light intensity of proximity pressure sensor assembly shown if FIG. 13 and a second bar that shows the detected light intensity of the same proximity pressure sensor assembly after reduction of the pressure responsivity of the proximity pressure sensor assembly.

FIG. 14 shows a bar graph with a first bar 174 that represents the saturated detected light intensity of a PPSA 134 and a second bar 176 that shows the detected light intensity of the same PPSA 134 after reduction of the pressure sensitivity of the PPSA 134. By reducing the pressure sensitivity of the saturated PPSA 134, the detected light intensity does not saturate the PPSA 134 and it becomes possible to monitor variation in the pressure applied on the PPSA 134. In FIG. 14, the pressure sensitivity has been adjusted to have the detected light intensity at the half value of the maximum value (maximum measurable value). However, this need not be the case. The pressure sensitivity can be adjusted to have the detected light intensity at any target value such as, for example, one quarter, one third, three eights, etc. of the maximum value.

In situations where the individual is a light individual that applies a pressure in the portion 170 that causes the PPSAs 134 in the portion 170 to have a low detected light intensity, the pressure sensitivity of the PPSAs 134 can be increased by increasing the light intensity generated by the respective light emitters 136 by increasing the electrical current powering the light emitters 136.

To do so, the pressure sensor monitor 110 is configured to detect which PPSAs 134 are experiencing low light levels on their light detectors 138. The pressure monitor sensor 110 can subsequently instruct the controller 112 to increase the pressure sensitivity of the PPSAs 134 that are experiencing the low light level situation.

Figure 15:
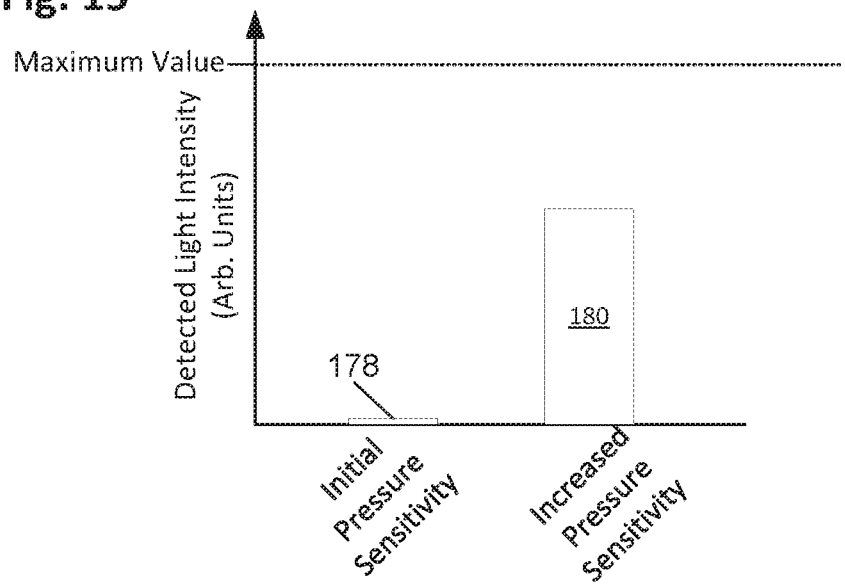
FIG. 15 a bar graph with a first bar that represents the low detected light intensity of a proximity pressure sensor assembly shown in FIG. 13 and a second bar that shows the detected light intensity of the same proximity pressure sensor assembly after increasing the pressure sensitivity of the proximity pressure sensor assembly.

FIG. 15 shows a bar graph with a first bar 178 that represents the low detected light intensity of a PPSA 134 and a second bar 180 that shows the detected light intensity of the same PPSA 134 after increasing the pressure sensitivity of the PPSA 134. By increasing the pressure sensitivity of the PPSA 134 that produces a low detected light intensity, it becomes possible to monitor smaller variation in the pressure applied on the PPSA in question. In FIG. 15, the pressure sensitivity has been adjusted to have the detected light intensity at a bit more than half of the maximum value (maximum measurable value). However, this need not be the case. The pressure sensitivity can be adjusted to have the detected light intensity at any target value such as, for example, one quarter, one third, three eights, etc. of the maximum value.

The monitored pressure at the PPSAs 134, or more generally, at the pressure sensors 106 shown in relation to some of the embodiments described above, will depend on the sampling rate at which the PPSAs 134 or pressure sensors 106 are monitored and on vital signs or health metric of the individual 160 resting on the PSM 102. For example, if the vital sign of interest is the breathing rate of the individual 160, then monitoring the pressure sensors at a rate of 1 Hz or more can be used to monitor breathing rates of 12 to 20 breaths per minute. In another example, if the vital sign of interest is the heart rate of the individual 160, then monitoring the pressure at a rate of 4 Hz can be used to monitor heart rates of 60 to 90 beats per minute. Any suitable sampling rate can be used provided it is the same or greater than the frequency of the signal being measured.

It is common for the individual 160 to move on the PSM 102 during monitoring of the individual's vital signs or other health metric. Because of such movements, baseline values of the monitored pressure and, in some cases, the monitored pressure on some pressure sensors can become saturated, which requires the pressure sensitivity of the saturated pressure sensors 106 to be reduced. In other cases, upon movement of the individual 160, the monitored pressure can become very low, which can require the pressure sensitivity of the related pressure sensors to be increased.

The inventors have discovered how to adjust, automatically and dynamically, the pressure sensitivity of the pressure sensors 106 to account for movements of the individual 160 on the PSM 102, i.e., to account for variations in baseline values of the monitored pressure on the pressure sensors. The following describes examples of how the pressure responsivity and be adjusted.

Figure 16:
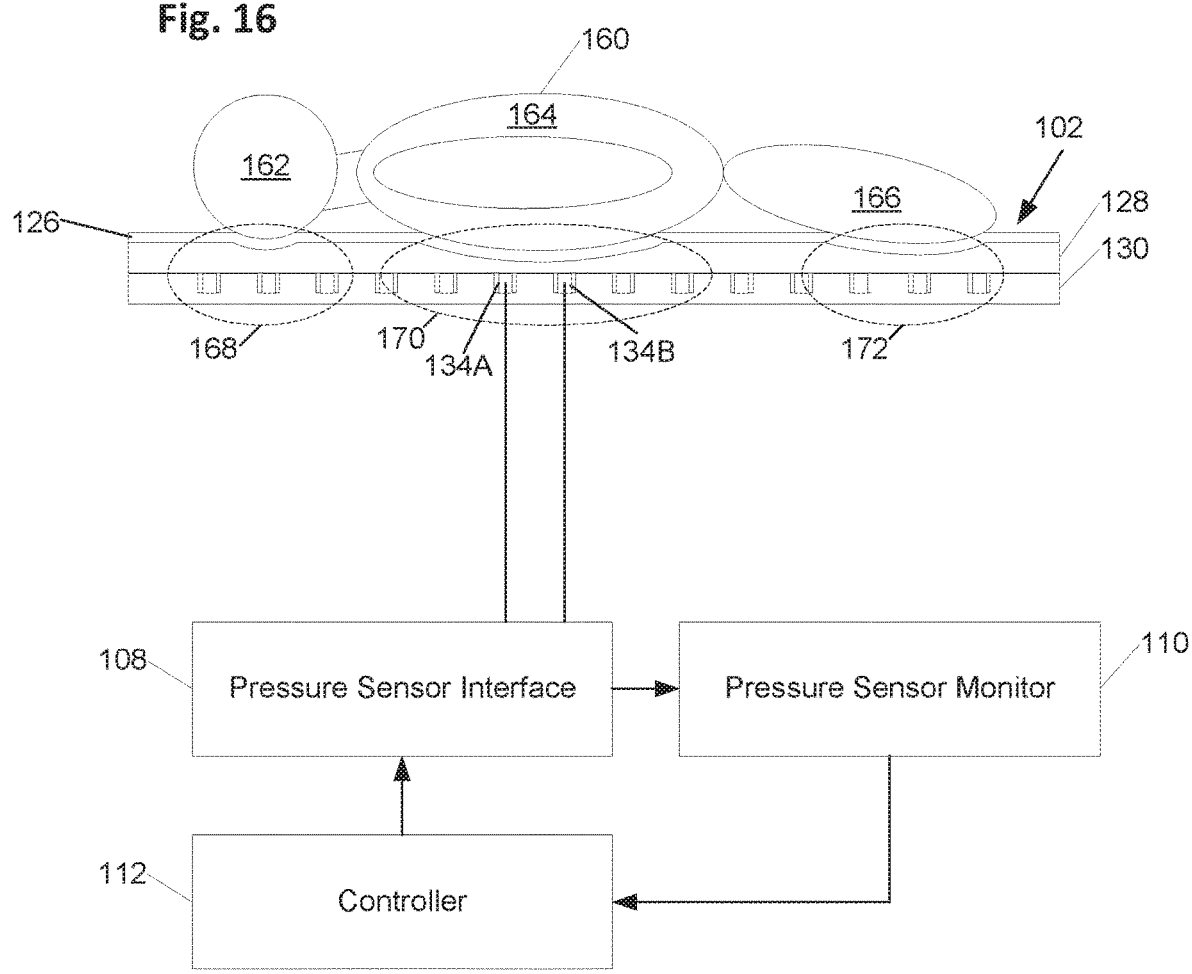
FIG. 16 shows the embodiment of FIG. 13 but with only two proximity pressure sensor assemblies, of the same portion of the pressure sensitive mat, coupled to the pressure sensor interface.

FIG. 16 shows the embodiment of FIG. 13 but with only two PPSAs 134A and 134B coupled to the pressure sensor interface 108. These two PPSAs 134A and 134B are in the same portion 170 of the PSM 102 and are close to one another. As such, it can be reasonably expected that the PPSAs 134A and 134B will be subjected to similar pressures and to similar pressure variations caused by movement of the individual 160.

Figure 17:
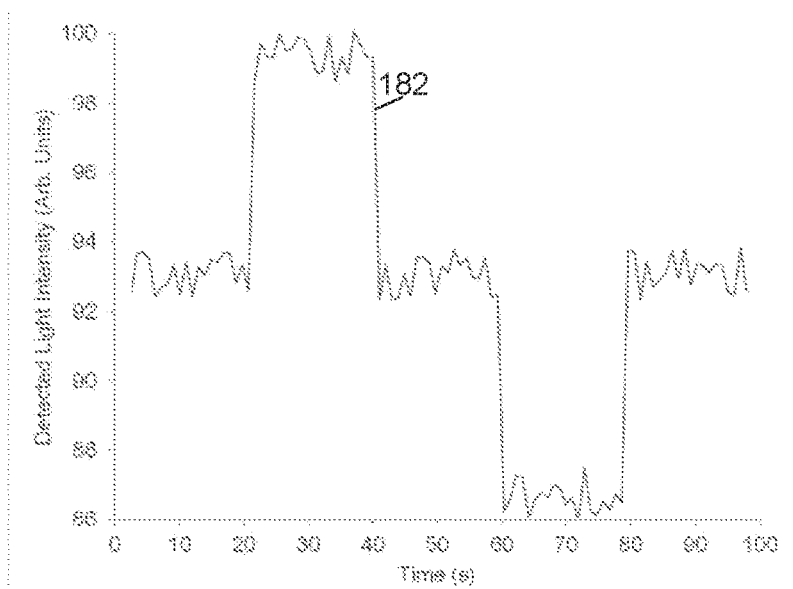
FIG. 17 shows a plot of detected light intensity as a function of time for one of the proximity sensor assemblies shown in FIG. 16.
Figure 18:
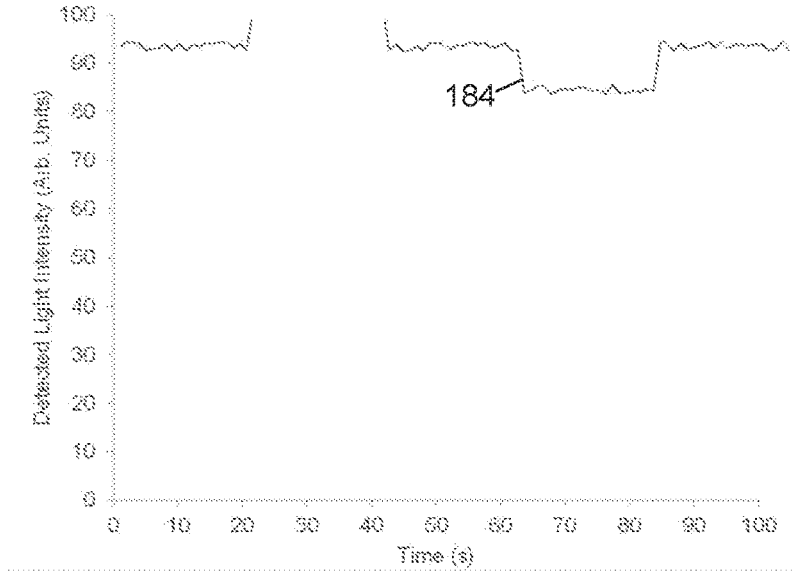
FIG. 18 shows a plot of detected light intensity as a function of time for another one of the proximity pressure sensor assemblies shown in FIG. 16.

As an example, FIG. 17 shows a plot 182 of detected light intensity as a function of time for PPSA 134A and FIG. 18 shows a plot 184 of detected light intensity as a function of time for PPSA 134B. As shown in FIG. 17, the detected light intensity on PPSA 134A ranges between 86 and 100, with the average being about 95. In FIG. 18, the detected light intensity of PPSA 134B is of the same order as that shown in FIG. 17, but saturates between the 21 second mark and the 41 second mark.

Figure 19:
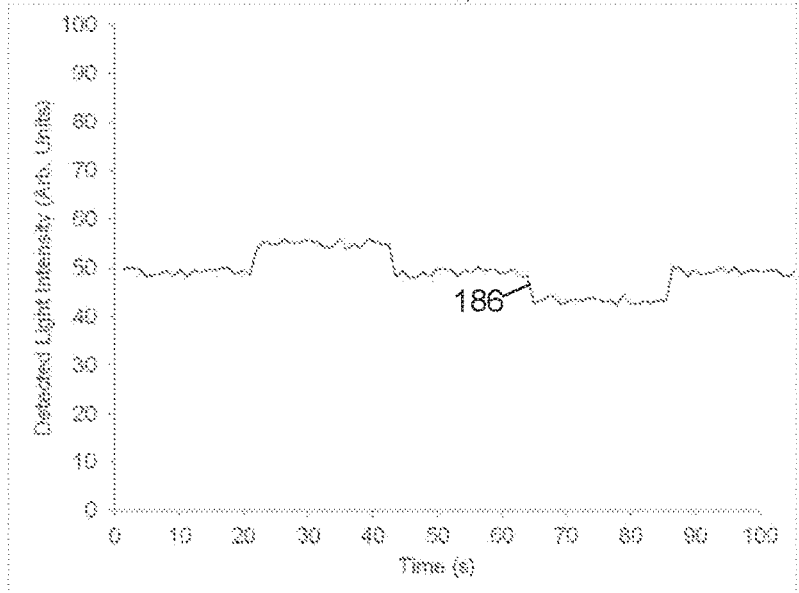
FIG. 19 shows a plot of detected light intensity as a function of time for the same proximity pressure sensor assembly as in FIG. 18, but after decreasing the pressure responsivity of the proximity pressure sensor assembly in question.

By monitoring the detected signal at PPSA 134A and by adjusting the pressure responsivity on PPSA 134B accordingly, the situation observed in plot 184 of FIG. 18 can be avoided. For example, by averaging the detected signal at PPSA 134A, it is possible to determine, within the first 10 seconds or so that the signal has an average value of about 95 on PPSA 134A, which is close to the top limit (100) of the range of the PPSA 134A. If the PPSA 134B has the same initial pressure responsivity setting as that of the PPSA 134B, then the pressure sensor monitor 110 can be configured to have the pressure responsivity of the PPSA 134B decreased, thereby avoiding the clipped detected light signal of plot 184. Instead, with reference to FIG. 19, the non-clipped plot 186 can be obtained. In the present example, by obtaining the average of 95 for the PPSA 134A, and by having previous knowledge that the available signal range is between 0 and 100, the responsivity of the PPSA 134B can be reduced to have a signal at the PPSA 134B that will have an average that is mid-range, i.e., that has a value of about 50, as shown in FIG. 19. Alternatively, the responsivity of the PPSA 134B can be adjusted to any suitable value, provided the detected intensity does not saturate the detector 138 or, does not produce very low, unusable detected intensity signal.

The average can be obtained by any suitable calculation that calculates a single value that represents the detected light intensity values. As examples, the average can be an arithmetic mean, a median, a mode, etc. The average can be calculated in accordance with any suitable number of detected light intensity values.

As will understood by the skilled worker, conditions on when to adjust the pressure responsivity of PPSA 134B as a function of the calculated average of the detected light intensity values of PPSA 134A can be pre-defined in the pressure monitor 110. For example the pressure monitor 110 may be configured to have the pressure responsivity of the PPSA 134B adjusted when the average varies by more than a preset, threshold value such as, for example, 10%, 20%, 40%, etc. In some embodiments, the average can be calculated over different time scales such as a few minutes (e.g., 1 to 10 minutes or more), a few seconds (e.g., 1 to 20 seconds or more), a few tenths of seconds (0.1 second to 1 second), etc. The averages calculated based on a larger time scale can account for body motion with respect to the PSM 102. The averages based on a shorter time scale can account for body motion within, for example, a breathing cycle.

In other embodiments, instead of adjusting the pressure responsivity of the PPSA 134B in accordance with an average value associated with PPSA 134A, the pressure monitor can apply any suitable filtering to the detected light intensities of PPSA 134A and adjust the pressure responsivity of the PPSA 134B in accordance with the filtered value.

In yet other embodiments, instead of adjusting the pressure responsivity of the PPSA 134B in accordance with an average value associated with PPSA 134A, the pressure monitor 110 perform any suitable analysis of the measured light intensities of PPSA 134A and can adjust the pressure responsivity of the PPSA 134B in accordance with the analysis result.

Figure 20:
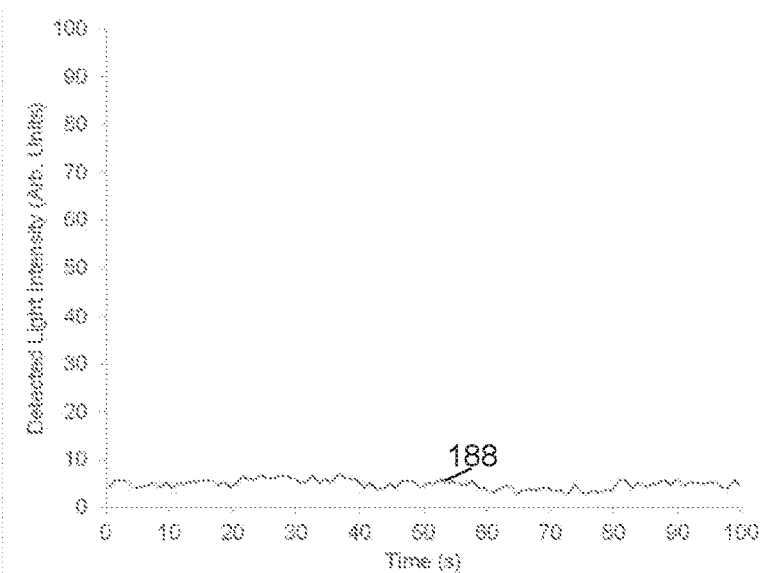
FIG. 20 shows a plot of detected light intensity as a function of time for one of the proximity sensor assemblies shown in FIG. 16.
Figure 21:
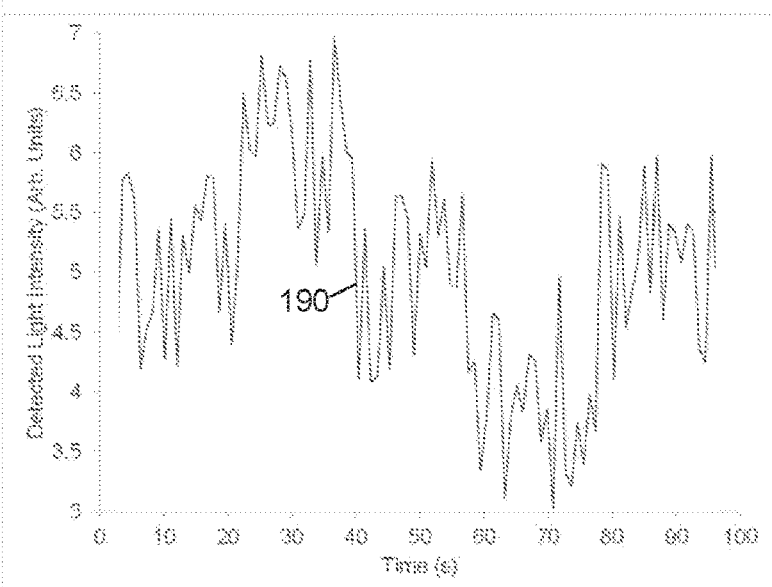
FIG. 21 shows a plot of detected light intensity as a function of time for another one of the proximity pressure sensor assemblies shown in FIG. 16.
Figure 22:
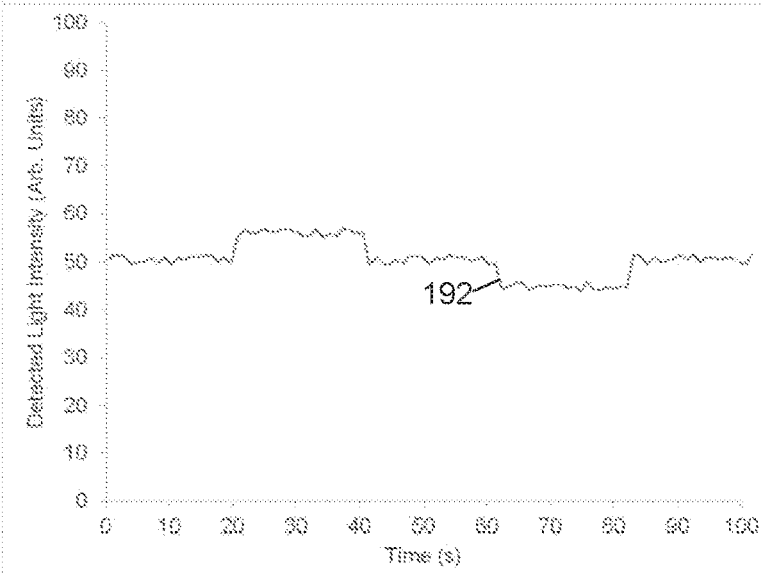
FIG. 22 shows a plot of detected light intensity as a function of time for the same proximity pressure sensor assembly as in FIG. 21, but after increasing the pressure responsivity of the proximity pressure sensor assembly in question.

FIGS. 20-22 relate to another example of how to use the signal detected at one PPSA 134 to control the responsivity of another PPSA 134. FIG. 20 shows a plot 188 of the detected light intensity at PPSA 134A and FIG. 21 shows a plot 190 of the detected light intensity at PPSA 134B. Plot 188 indicates a low long term average detected signal at PPSA 134A while plot 190 shows subtle changes in the detected intensity and a lot of noise at PPSA 134B. Based on the average detected value obtain from PPSA 134A, the pressure responsivity of PPSA 134B can be increased to obtain a detected intensity on PPSA 134A that has a greatly improved signal to noise ratio, as shown in plot 192 of FIG. 22. In the example of FIG. 22, the responsivity is such that the average detected light intensity at PPSA 134B is about 50. This need not be the case in that the responsivity can be adjusted to have an average detected light intensity at PPSA 134B that produces a usable signal.

Figure 23:
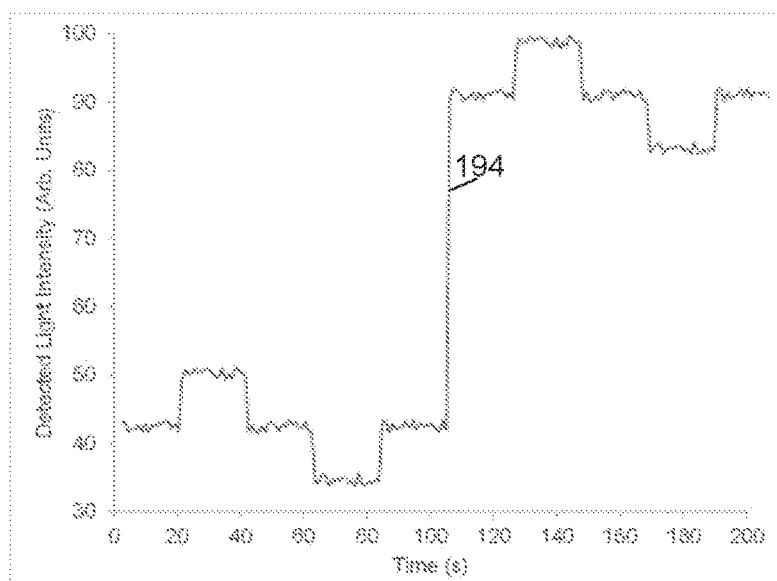
FIG. 23 shows a plot of detected light intensity as a function of time for one of the proximity sensor assemblies shown in FIG. 16.
Figure 24:
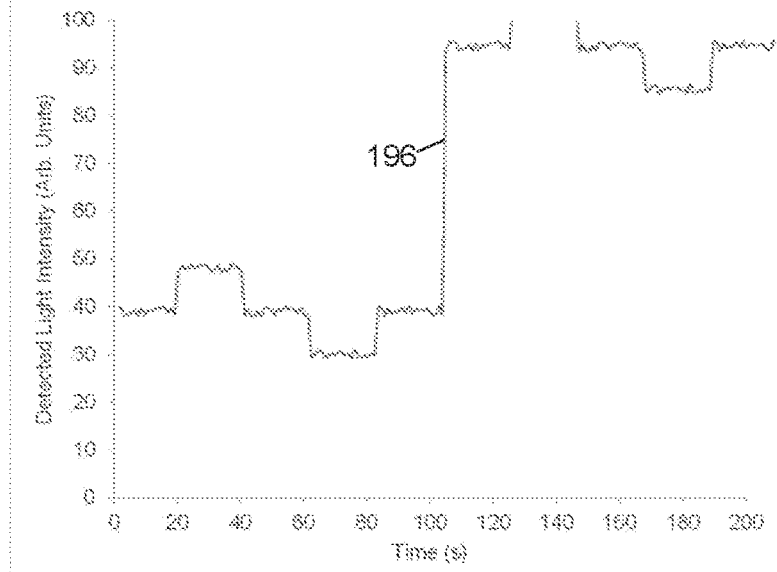
FIG. 24 shows a plot of detected light intensity as a function of time for another one of the proximity pressure sensor assemblies shown in FIG. 16.
Figure 25:
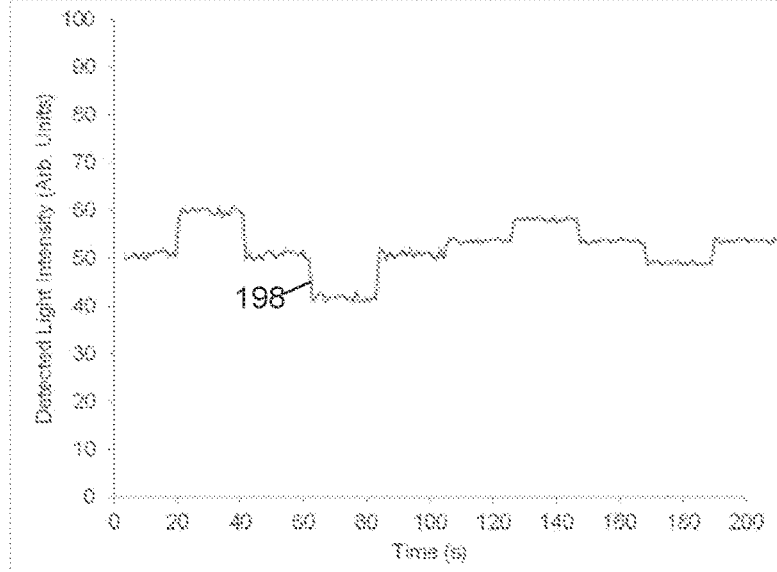
FIG. 25 shows a plot of detected light intensity as a function of time for the same proximity pressure sensor assembly as in FIG. 21, but after decreasing, at about the 100 second mark, the pressure responsivity of the proximity pressure sensor assembly in question.

FIGS. 23-25 relate to another example of how to use the signal detected at one PPSA to control the responsivity at another PPSA. FIG. 23 shows a plot 194 the detected light intensity at PPSA 134A, which increases significantly, due to movement of the individual 160, at about the 108 second mark. PPSA 134B, which aims to monitor vital signs or other health metrics, also experiences the same step change in its detected light intensity, as shown in the plot 196 of FIG. 24. In FIG. 24, because of the change of position of the individual 160 and the ensuing increase in average pressure, the monitored pressure signal saturates between about 130 seconds and about 150 seconds. To avoid this loss of information, the pressure sensitivity of PPSA 134B can be decreased when such a step in the monitored signal at 134A is detected. The resulting monitored signal is shown at plot 198 of FIG. 25, where the pre-step signal has a different variation in amplitude than in the post-step signal. As will be understood by the skilled worker, the data of plot 198 can be processed in any suitable way to obtain similar amplitude variations before and after the ~130 second mark.

Generally, the pressure responsivity of the PPSA 134B can be adjusted by analyzing detected light intensities of the PPSA 134A to obtain an analysis result and by using the analysis result to determine if an adjustment of the pressure responsivity of the PPSA 134B is required and, when it is determined that the pressure responsivity is to be adjusted, determining an adjustment value as a function of the analysis result. The analysis can include calculating an average value of the detected light intensities of the PPSA 134A, determining a variation in consecutive detected light intensities of the PPSA 134A that exceed a pre-determined threshold, filtering the detected light intensities of the PPSA 134A, calculating a derivative value of the detected light intensities of the PPSA 134A, etc.

Figure 26:
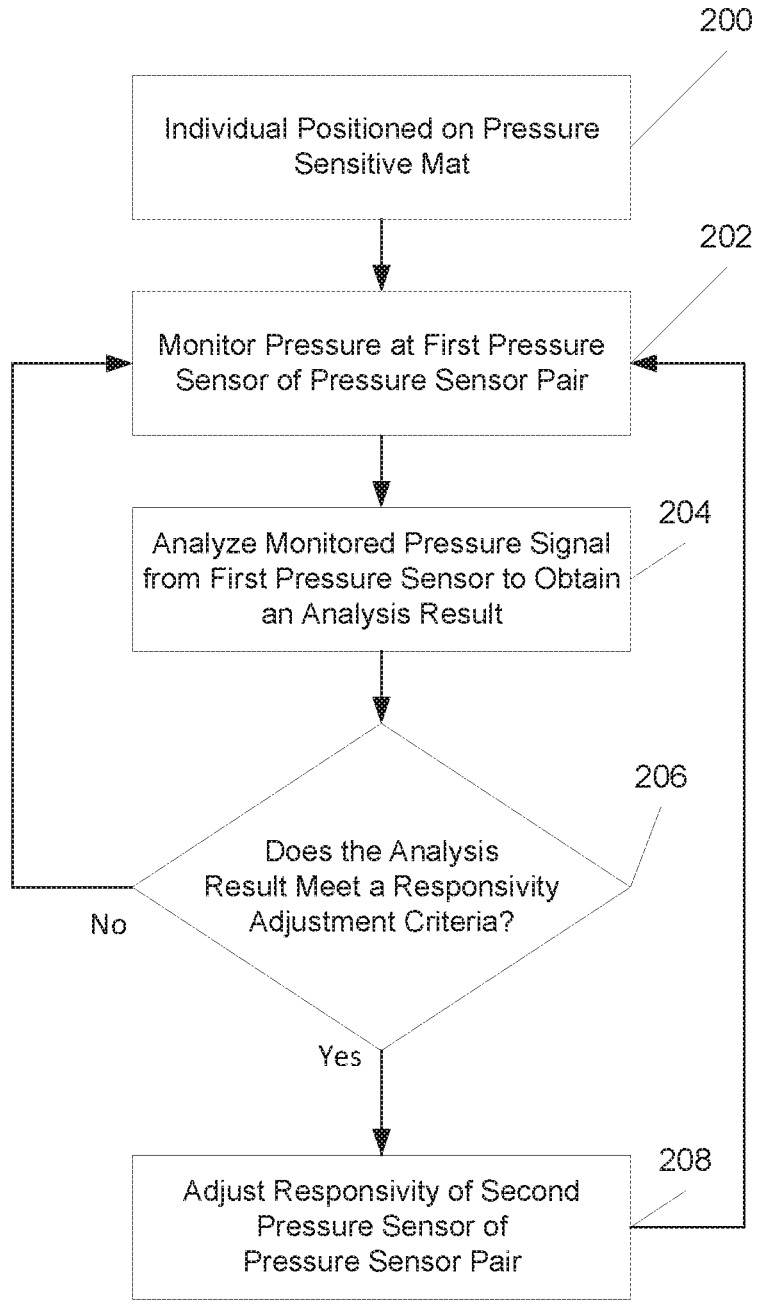
FIG. 26 shows a flowchart of an embodiment of a method of adjusting the responsivity of a pressure sensor as a function of the pressure monitored at another pressure sensor, in accordance with the present disclosure.

FIG. 26 shows a flowchart of an embodiment of a method of adjusting the responsivity of a pressure sensor as a function of the pressure monitored at another pressure sensor. An individual is positioned on a PSM at step 200. At step 202, the pressure at a first pressure sensor of the PSM is monitored to obtain a monitored pressure signal from the first pressure sensor. At step 204, the monitored pressure signal from the first pressure sensor is analyzed to obtain an analysis result. At step 206, a determination is made of whether or not the analysis result meets a responsivity adjustment criteria. If step 206 determines that no adjustment is required, the method proceeds back to step 202. If step 206 determines that an adjustment of the responsivity is required, then the method proceed to step 208, where the responsivity of the second pressure sensor is made.

The analysis at step 204 can take various forms. In some embodiments, the analysis of the pressure signal from the first pressure sensor can include calculating an average value of the monitored pressure signal from the first pressure sensor. In another embodiment, the analysis can include calculating a difference between consecutive monitored pressure signal values of the monitored pressure signal from the first pressure sensor. In another embodiment, the analysis can include determining a maximum value of the monitored pressure signal of the monitored pressure signal from the first pressure sensor over a preset period. In another embodiment, the analysis can include determining a minimum value of the monitored pressure signal from the first pressure sensor over a preset period. In another embodiment, the analysis can include calculating a derivate value of the monitored pressure signal from the first pressure sensor.

Step 206 can determine if the analysis result warrants an adjustment of the responsivity of the second pressure sensor, and by how much, by evaluating the analysis result obtained at 204 in accordance with pre-determined rules. In essence, step 206 is to determine if the second pressure sensor, with its pressure responsivity set as it is, is likely to be saturated or if it is likely to measure pressure with a signal to noise ratio so low that no useful vital sign data or health metric data can be extracted. In some embodiments, the pre-determined rules will evaluate the analysis result by comparing the analysis result to a preset target value. An example of the evaluation is as follows in the case where the analysis result is an average value of the monitored signal at the first pressure sensor and the preset target value is a target average of the monitored signal at the first pressure sensor:

Is the analysis result greater than the preset target value?

If so, and if the analysis result is an average value of the monitored signal at the first pressure sensor, then decrease the pressure responsivity of the second pressure sensor by a factor equal to the target value based on the analysis value.

In another example, if the analysis result is an average and if the average is 10% higher than desired, then the light intensity of emitter can be reduced by 10%. In a further example, if the average is 10% higher than desired, the light intensity can be reduced by 8% (or any other suitable value). In other examples, the relationship between the analysis result (e.g., an average) and the adjustment of the light intensity can be a linear relationship or a quadratic relationship or an exponential relationship.

The target value can indicate if the responsivity of the second pressure sensor is to be increased or decreased.

Figure 27:
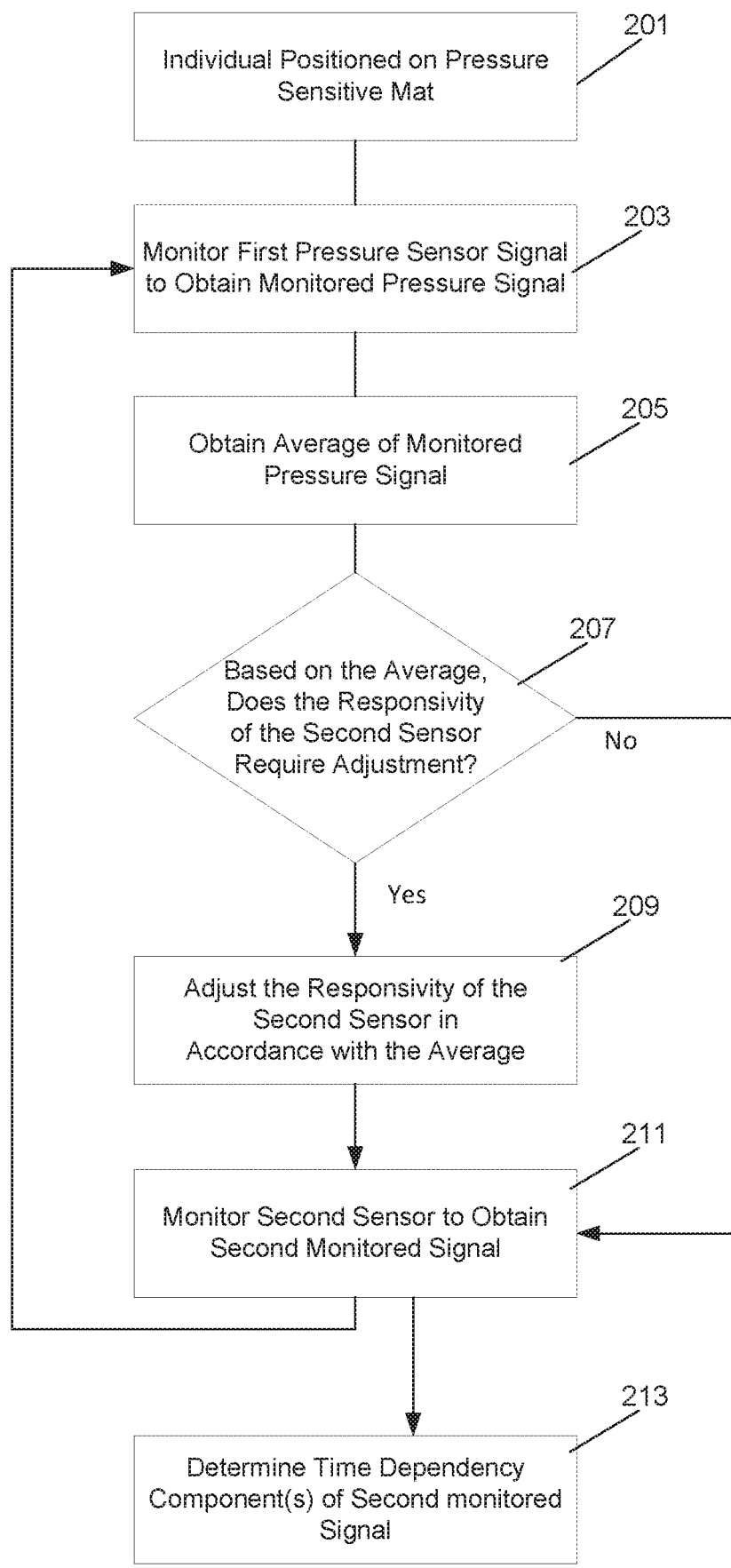
FIG. 27 shows a flowchart of another embodiment of a method of adjusting the responsivity of a pressure sensor as a function of the pressure monitored at another pressure sensor, in accordance with the present disclosure.

FIG. 27 shows a flowchart of an embodiment of a method of adjusting the responsivity of a pressure sensor as a function of the pressure monitored at another pressure sensor. An individual is positioned on a PSM at step 201. At step 203, the pressure at a first pressure sensor of the PSM is monitored to obtain a monitored pressure signal from the first pressure sensor. At step 205, the monitored pressure signal from the first pressure sensor is analyzed to obtain an average of the monitored pressure signal. At step 207, a determination is made of whether or not the obtained average warrants a responsivity adjustment. If step 207 determines that no adjustment is required, the method proceeds to step 211, where the pressure at the second pressure sensor is monitored. If step 207 determines that an adjustment of the responsivity is required, then the method proceed to step 209, where the responsivity of the second pressure sensor is made. Subsequently, the method proceeds to step 211, where the pressure at the second pressure sensor is monitored. A time dependency analysis of the signal monitored at the second pressure sensor can be carried out at step 213.

As shown in the context of some embodiments described above, in PSMs that use PPSAs 134 as pressure sensors, the pressure sensitivity can be controlled by controlling the current that powers the emitter of the PPSAs.

In PSMs that use force sensitive resistors as pressure sensors, the force responsivity of the force sensitive resistors can be controlled through voltage divider circuitry that includes a digital potentiometer that has a computer-controlled resistor.

In PSMs that use fiber optic pressure sensors as pressure sensors, the pressure sensitivity can be controlled similarly as in embodiments where PPSAs are used.

Returning to embodiments where PPSAs are used to monitor vital signs or other health metrics, instead of controlling the pressure sensitivity of a single PPSA as a function of detected light intensities at a nearby PPSA, it is possible to control the pressure sensitivity of multiple PPSAs as a function of the detected light intensities at the nearby PPSA. In some embodiments, the multiple PPSAs can each be adjusted to monitor a different health metric; for example, one of PPSAs monitors the breathing rate while another of the PPSAs monitors the heart rate.

Figure 28:
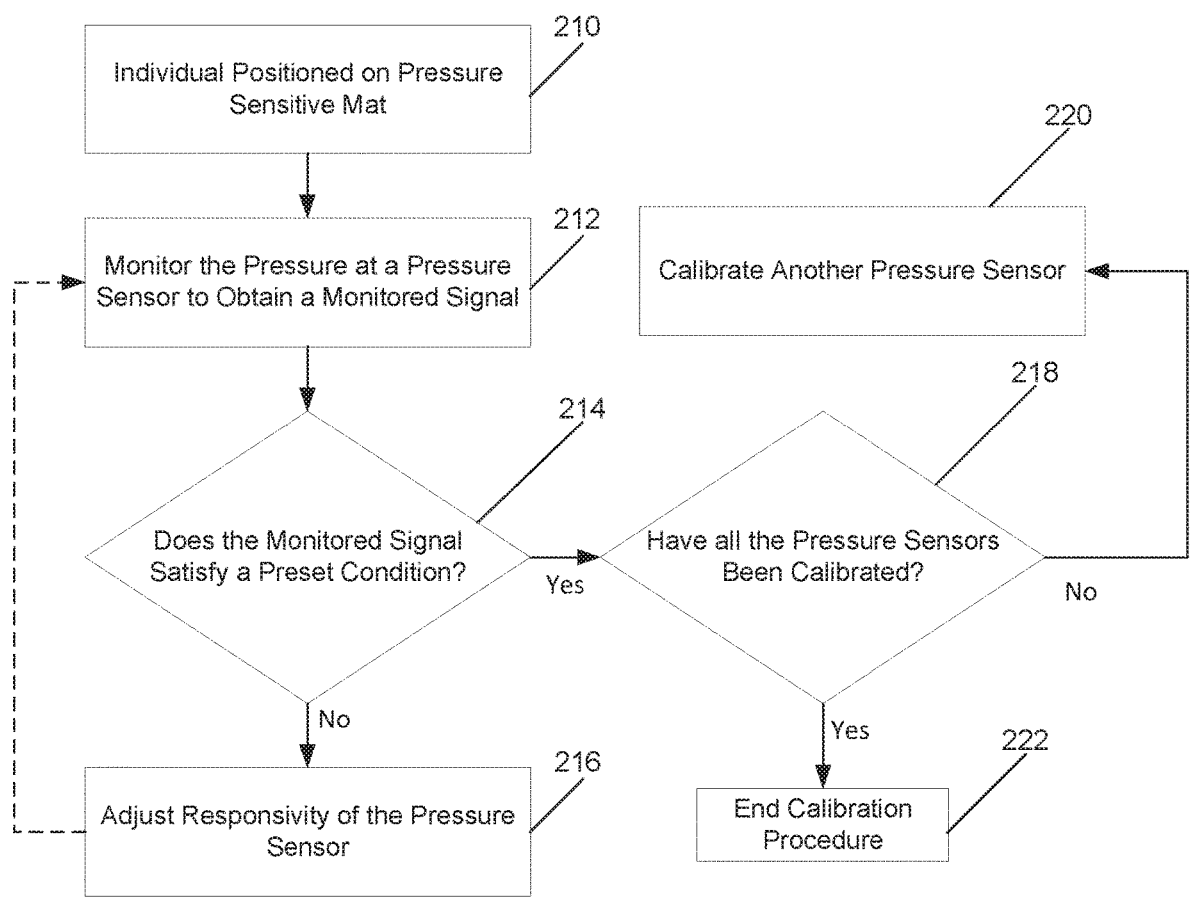
FIG. 28 shows a flowchart of an embodiment of a calibration procedure of a system for monitoring vital signs or other health metrics of an individual, in accordance with the present disclosure.

In some embodiments, systems that use PSMs in accordance with the present disclosure require calibration prior to monitoring vital signs or other health metrics of an individual positioned on the PSM. FIG. 28 shows a flowchart of an embodiment of a calibration procedure of such systems. At step 210, the individual is positioned on the PSM. At step 212, the pressure at each pressure sensor is monitored to obtain monitored pressure signals. At step 214, on a pressure sensor by pressure sensor basis, a determination is made whether or not to monitored signal satisfies a preset condition. Step 214 can include determining if each sensor signal is saturated or is close to saturation. Step 214 can also include determining if each sensor signal is below a threshold value. If step 214 determines that the monitored signal does not satisfy the present condition, then the responsivity of the respective pressure sensor is adjusted at step 216. Optionally, step 216 can loop back to step 212 to ensure that adjustment to the responsivity does provide a monitored signal that satisfies the preset condition. If step 214 determines that the preset condition is met, then the calibration procedure proceeds to step 218 where it is determined if all the pressure sensors have been calibrated. If not all the pressure sensors have been calibrated, then the calibration procedure proceeds to step 220, where an un-calibrated pressure sensor is calibrated. If all the pressure sensors have been calibrated, then calibration procedure ends at step 222.

Figure 29:
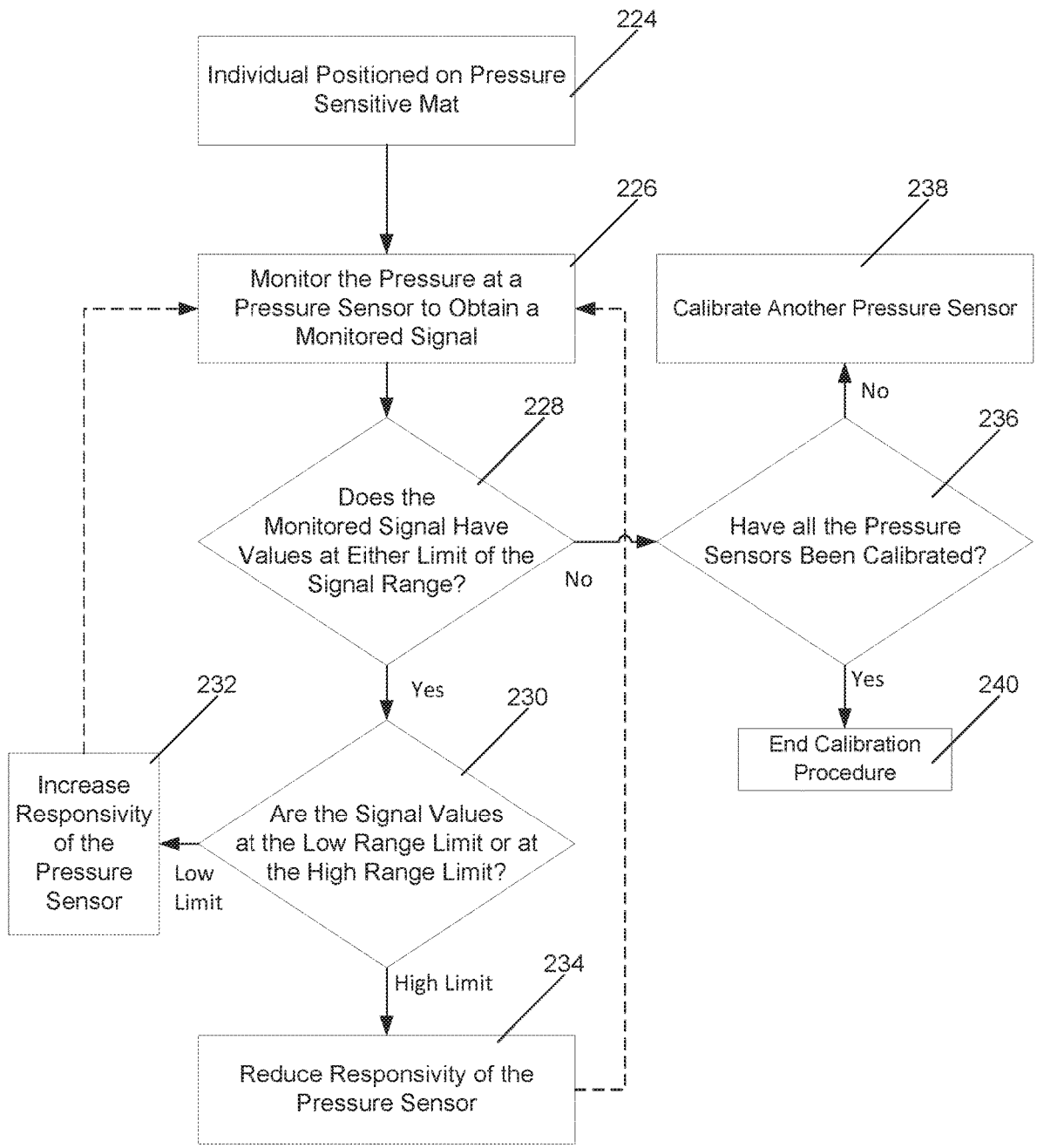
FIG. 29 shows a flowchart of another embodiment of a calibration procedure of a system for monitoring vital signs or other health metrics of an individual, in accordance with the present disclosure.

FIG. 29 shows a flowchart of another embodiment of a calibration procedure. At step 224, the individual is positioned on the PSM. At step 226, the pressure at a pressure sensor is monitored to obtain a monitored pressure signal. At step 228, a determination is made whether or not to monitored signal has values at the lower limit or at the higher limit of the pressure sensor signal range. If the monitored signal does have values at the lower limit or at the higher limit of the pressure sensor signal range, the calibration procedure proceeds to step 230, where a determination is made with respect to the values being at the lower limit or at the high limit. If the values are the lower limit, the calibration procedure proceeds to step 232, where the responsivity of the pressure sensor is increased and, subsequently, the procedure loops back to step 226. Going back to step 230, if the values are at the higher limit, the calibration procedure proceeds to step 234, where the responsivity of the pressure sensor is decreased and, subsequently, the procedure loops back to step 226.

When step 228 determines that no, the monitored signal does not have values at either limit of the signal range, the calibration procedure proceeds to step 236 to determine if all the pressure sensors have been calibrated. If not all the pressure sensors have been calibrated, then the calibration procedure proceeds to step 238, where an un-calibrated pressure sensor is calibrated. If all the pressure sensors have been calibrated, then calibration procedure ends at step 240.

Optionally, steps 232 and 234 can loop back to step 226 to ensure that adjustment to the responsivity does provide a monitored signal that does not have values at either limit of the signal range.

Embodiments of the PSM of the present disclosure can be used in long-term care facilities and hospitals to monitor health metrics of patients. In these embodiments, the PSM can be placed on the patient's bed (above or below the bed's mattress). In similar embodiments, the PSM of the present disclosure can be used in the homes of aging individuals that live independently but have health concerns. Other embodiments can use the PSM of present disclosure to monitor health metrics of infants by installing the PSM in the infant's crib. Other embodiments of the PSM of the present disclosure can be used with chairs, wheel chairs, or vehicle seats instead of mattresses. In yet other embodiments of the PSM of the present disclosure, the PSM can be used to monitor health metrics of aging adults that have illnesses or a decline in health associated with chronic health issues such as congestive heart failure, dialysis, epilepsy, etc.

Advantageously, the embodiments of the PSM and PSM system of the present disclosure allows for a single, calibratable pressure sensor to be used to in multiple health metric monitoring scenarios for individuals of different masses. As such, this provides a considerable cost advantage over prior art PSM and PSM systems. Further, the PSM and PSM system of the present disclosure, with their calibratable pressure sensors, allows for the accurate monitoring of small pressure variation signals buried in larger amplitude signals.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration Information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A system for monitoring health metrics of an individual, the system comprising:
   a mat;
   a plurality of pressure sensors coupled to the mat, the plurality of pressure sensors configured to generate a respective plurality of pressure signals when the individual is positioned on the mat and applies a pressure to the mat, each pressure sensor of the plurality of pressure sensors having a respective pressure responsivity configured to be modified by varying an electrical parameter of the respective pressure sensor, each pressure sensor of the plurality of pressure sensors including a proximity sensor assembly with a light emitter and a light detector, the electrical parameter of each pressure sensor being a current of the light emitter; and
   circuitry coupled to the plurality of pressure sensors, the circuitry configured to:
      monitor a first pressure signal generated by a first pressure sensor of the plurality of pressure sensors, to obtain a first monitored signal;
      in accordance with the first monitored signal and in accordance with pre-determined rules, vary the electrical parameter of a second pressure sensor of the plurality of pressure sensors, to obtain a modified pressure responsivity; and
      monitor a second pressure signal generated by the second pressure sensor that has the modified pressure responsivity, the monitored second pressure signal being associated with at least one of the health metrics of the individual,
   the mat having:
      a top layer configured to reflect light emitted by the light emitter;
      a compressible layer coupled to the top layer, the compressible layer configured to be compressed upon pressure being applied thereto and further configured to transmit the light emitted by the light emitter; and
      a bottom layer coupled to the compressible layer and spaced apart from the top layer by the compressible layer, the bottom layer having the plurality of pressure sensors secured thereto,
   the plurality of pressure sensors including a first group of pressure sensors and a second group of pressure sensors, and, when the individual is not applying pressure on the mat, each pressure sensor of the first group of pressure sensors is spaced apart from the top layer by a first distance, each pressure sensor of second group of pressure sensors being spaced apart from the top layer by a second distance, the second distance being different from the first distance.

2. The system of claim 1, wherein the circuitry is configured to vary the electrical parameter of the second pressure sensor in accordance with the first monitored signal and in accordance with the pre-determined rules by analyzing the first monitored signal to obtain an analysis result and by evaluating the analysis result in accordance with the pre-determined rules.

3. The system of claim 2, wherein:
   analyzing the first monitored signal includes calculating an average value of the first monitored signal, and
   the analysis result is the average value.

4. The system of claim 3, wherein calculating an average value includes at least one of calculating:
   an arithmetic mean value;
   a median value; and
   a mode value.

5. The system of claim 1, wherein the plurality of the pressure sensors are arranged in a pattern, the pattern being a square pattern or a hexagonal pattern.

6. The system of claim 1, wherein the mat has a top surface and the plurality of pressure sensors are spaced apart from, and substantially parallel to, the top surface.

7. The system of claim 1, wherein the mat has two or more than two portions that have a different areal density of pressure sensors.

8. The system of claim 1, wherein the light emitter is configured to emit infrared light and the light detector is configured to detect infrared light.

9. The system of claim 1, wherein the bottom layer defines a plurality of recesses, each recess of the plurality of recessed having a pressure sensor of the plurality of sensor secured therein.

10. The system of claim 1, wherein:
   the first distance is greater than the second distance,
   the first distance is equal to a thickness of the compressible layer between the top layer and each pressure sensor of the first group of pressure sensors, and
   the second distance is equal to a thickness of the compressible layer between the top layer and each pressure sensor of the second group of pressure sensors.

11. The system of claim 1, wherein the monitored second pressure signal is associated with at least one of the heart rate of the individual and the breathing rate of the individual.

12. The system of claim 1, wherein the circuitry is further configured to
- in accordance with the first monitored signal and in accordance with the pre-determined rules, vary the electrical parameter of additional pressure sensors of the plurality of pressure sensors, to obtain a modified pressure responsivity; and
- monitor additional pressure signals generated by the additional pressure sensors that have the modified pressure responsivity, the monitored additional pressure signals also being associated with the at least one of the vital sign of the individual.

13. The system of claim 1, wherein the circuitry includes:
- a pressure sensor interface coupled to the plurality of pressure sensors;
- a pressure sensor monitor coupled to the pressure sensor interface, the pressure sensor monitor to monitor the plurality of pressure signals, to determine when to modify the pressure responsivity of the plurality of pressure sensors, and to generate a plurality of control signals associated with a modification of the pressure responsivity of each of the plurality of pressure sensors; and
- a controller coupled to the pressure monitor and to the pressure sensor interface, the controller to control the electrical parameter of each of the plurality of the pressure sensors, in accordance with the plurality of control signals.

14. A system for monitoring health metrics of an individual, the system comprising:
- a mat;
- a plurality of pressure sensors coupled to the mat, the plurality of pressure sensors configured to generate a respective plurality of pressure signals when the individual is positioned on the mat and applies a pressure to the mat, each pressure sensor of the plurality of pressure sensors having a respective pressure responsivity configured to be modified by varying an electrical parameter of the respective pressure sensor;
- circuitry coupled to the plurality of pressure sensors, the circuitry configured to:
  - monitor a first pressure signal generated by a first pressure sensor of the plurality of pressure sensors, to obtain a first monitored signal;
  - in accordance with the first monitored signal and in accordance with pre-determined rules, vary the electrical parameter of a second pressure sensor of the plurality of pressure sensors, to obtain a modified pressure responsivity; and
  - monitor a second pressure signal generated by the second pressure sensor that has the modified pressure responsivity, the monitored second pressure signal being associated with at least one of the health metrics of the individual, the circuitry configured to calibrate the plurality of pressure sensors to a weight of the individual when the individual is positioned on the mat, by performing the following actions:
  - monitoring a pressure signal generated by each pressure sensor of the plurality of pressure sensors, to obtain a plurality of monitored signals; and
  - in accordance with the plurality of monitored signals and in accordance with the pre-determined rules, vary the electrical parameter of each pressure sensor of the plurality of pressure sensors, to obtain a modified pressure responsivity for each pressure sensor of the plurality of pressure sensors.

15. The system of claim 14, wherein each pressure sensor of the plurality of pressure sensors includes a proximity sensor assembly with a light emitter and a light detector, the electrical parameter of each pressure sensor being a current of the light emitter.

16. The system of claim 15, wherein the mat has:
- a top layer configured to reflect light emitted by the light emitter;
- a compressible layer coupled to the top layer, the compressible layer configured to be compressed upon pressure being applied thereto and further configured to transmit the light emitted by the light emitter; and
- a bottom layer coupled to the compressible layer and spaced apart from the top layer by the compressible layer, the bottom layer having the plurality of pressure sensors secured thereto.

17. The system of claim 16, wherein the plurality of pressure sensors includes a first group of pressure sensors and a second group of pressure sensors, and, when the individual is not applying pressure on the mat, each pressure sensor of the first group of pressure sensors is spaced apart from the top layer by a first distance, each pressure sensor of second group of pressure sensors being spaced apart from the top layer by a second distance, the second distance being different from the first distance.

18. The system of claim 14, wherein the predetermined rules are set to obtain, for each pressure sensor of the plurality of pressure sensors, a respective modified pressure responsivity that causes each respective pressure sensor to generate a signal that is equal to a pre-determined ratio of a full signal range of the respective pressure sensor.

* * * * *